United States Patent
Shibayama et al.

(10) Patent No.: US 10,393,663 B2
(45) Date of Patent: Aug. 27, 2019

(54) SURFACE-ENHANCED RAMAN SCATTERING ELEMENT AND METHOD FOR MANUFACTURING SAME

(71) Applicant: HAMAMATSU PHOTONICS K.K., Hamamatsu-shi, Shizuoka (JP)

(72) Inventors: Katsumi Shibayama, Hamamatsu (JP); Masashi Ito, Hamamatsu (JP); Kazuto Ofuji, Hamamatsu (JP); Hiroki Oyama, Hamamatsu (JP); Yoshihiro Maruyama, Hamamatsu (JP); Nao Inoue, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/553,337

(22) PCT Filed: Feb. 10, 2016

(86) PCT No.: PCT/JP2016/053970
§ 371 (c)(1),
(2) Date: Aug. 24, 2017

(87) PCT Pub. No.: WO2016/136472
PCT Pub. Date: Sep. 1, 2016

(65) Prior Publication Data
US 2018/0136134 A1 May 17, 2018

(30) Foreign Application Priority Data

Feb. 26, 2015 (JP) .................................. 2015-036726

(51) Int. Cl.
*G01N 21/65* (2006.01)
*B82Y 15/00* (2011.01)

(52) U.S. Cl.
CPC ............ *G01N 21/658* (2013.01); *B82Y 15/00* (2013.01); *G01N 2021/651* (2013.01)

(58) Field of Classification Search
CPC ........... G01N 21/658; G01N 2021/651; B82Y 15/00; G01J 3/44
(Continued)

(56) References Cited

U.S. PATENT DOCUMENTS

| 2008/0297802 | A1 | 12/2008 | Ogawa et al. |
| 2011/0166045 | A1 | 7/2011 | Dhawan et al. |
| 2014/0043605 | A1* | 2/2014 | Tseng .................. G01N 21/658 356/301 |

FOREIGN PATENT DOCUMENTS

| CN | 101057132 A | 10/2007 |
| CN | 102103086 A | 6/2011 |

(Continued)

OTHER PUBLICATIONS

International Preliminary Report on Patentability dated Sep. 8, 2017 for PCT/JP2016/053970.
(Continued)

Primary Examiner — Hina F Ayub
(74) Attorney, Agent, or Firm — Drinker Biddle & Reath LLP

(57) ABSTRACT

An SERS element includes a substrate, a fine structure portion formed on a surface of the substrate and having a plurality of pillars, and a conductor layer formed on the fine structure portion and constituting an optical functional portion that causes surface-enhanced Raman scattering. A groove is provided in an outer surface of each pillar. A plurality of gaps are formed in the conductor layer by forming the conductor layer on the outer surface of each pillar in a state in which at least a portion of an inner surface of the groove is exposed.

14 Claims, 29 Drawing Sheets

(58) Field of Classification Search
USPC .......................................................... 356/301
See application file for complete search history.

(56) References Cited

FOREIGN PATENT DOCUMENTS

| | | |
|---|---|---|
| JP | 2009-222507 A | 10/2009 |
| JP | 2011-033518 A | 2/2011 |
| JP | 2015-014545 A | 1/2015 |
| JP | 2015-014546 A | 1/2015 |
| JP | 2015-014547 A | 1/2015 |
| WO | WO-2014/025027 A1 | 2/2014 |
| WO | WO-2014/025030 A1 | 2/2014 |
| WO | WO-2014/025035 A1 | 2/2014 |

OTHER PUBLICATIONS

"Q-SERS™ G1 Substrate URL:http://www.optoscience.com/maker/nanova/pdf/QSERS_G1.pdf", Opto Science, Inc., retrieved Jul. 19, 2012.

* cited by examiner

Fig.6
(a)
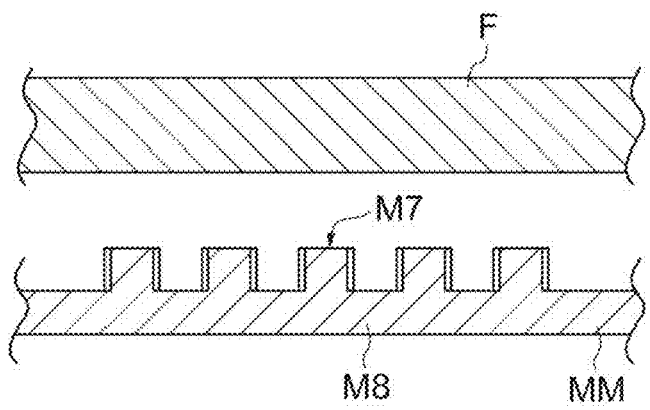
(b)
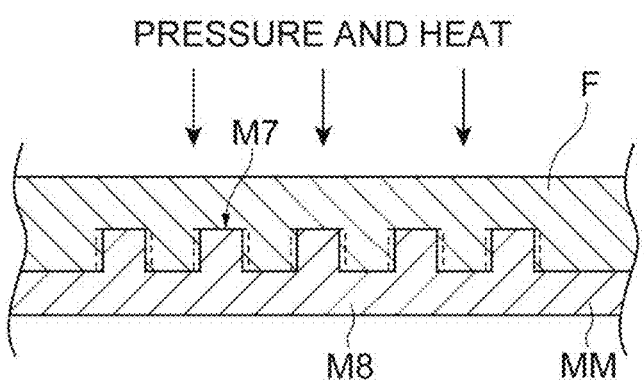
(c)
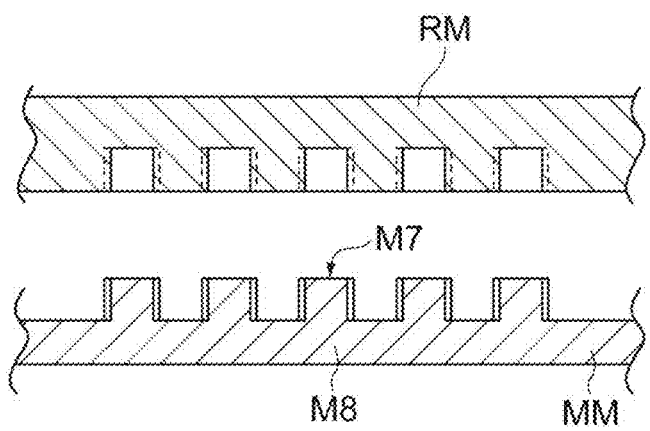

Fig.7
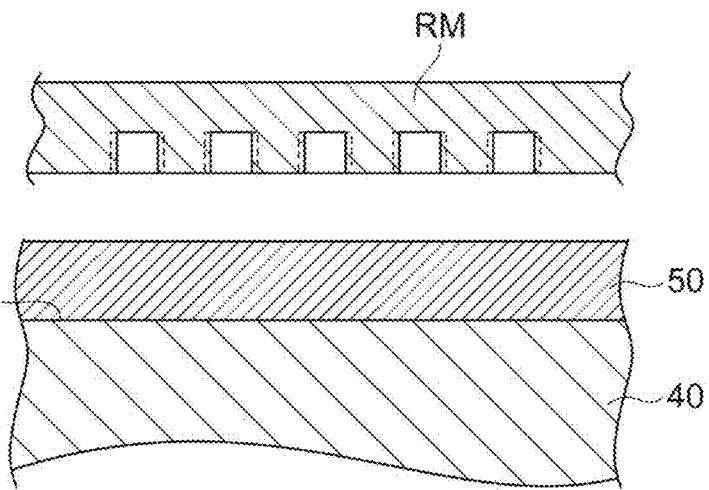
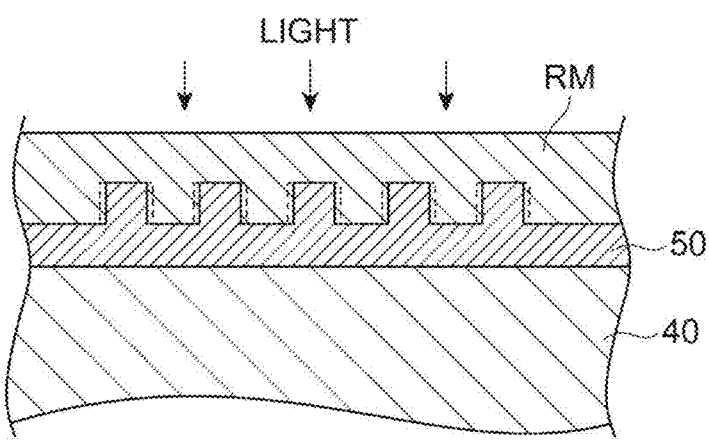
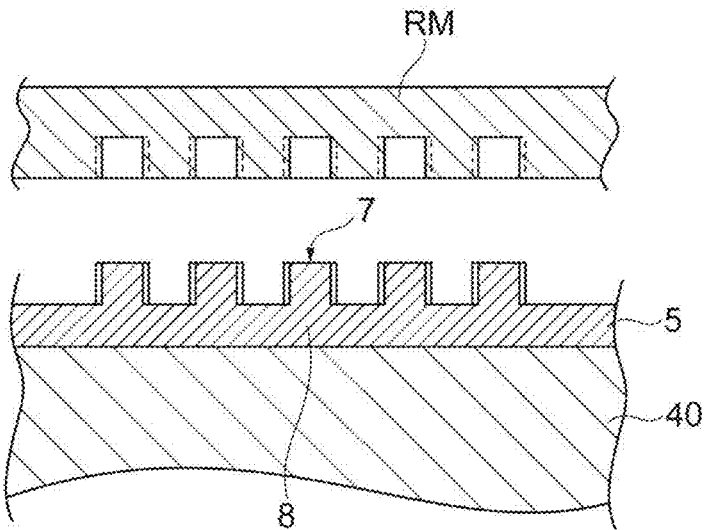

Fig.9
(a) 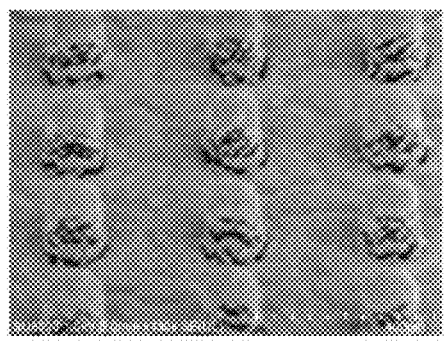
(b) 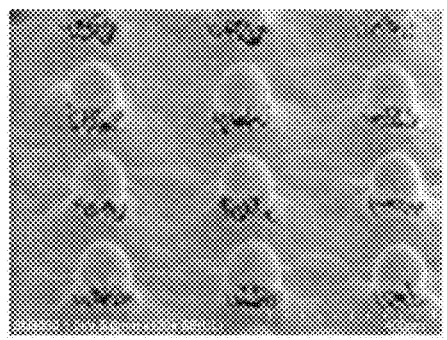

*Fig.13*
(a)
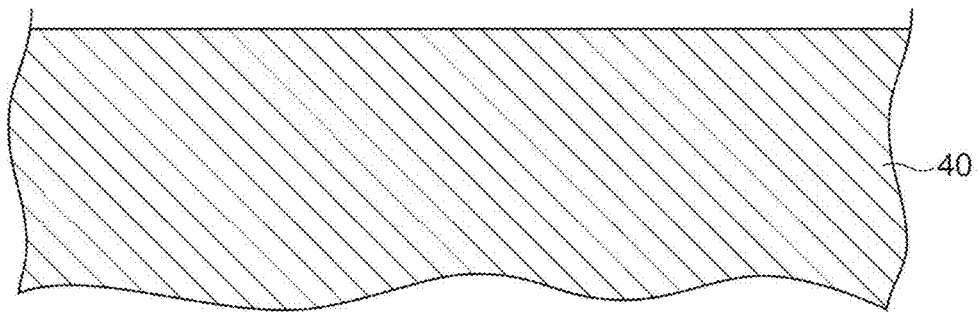
(b)
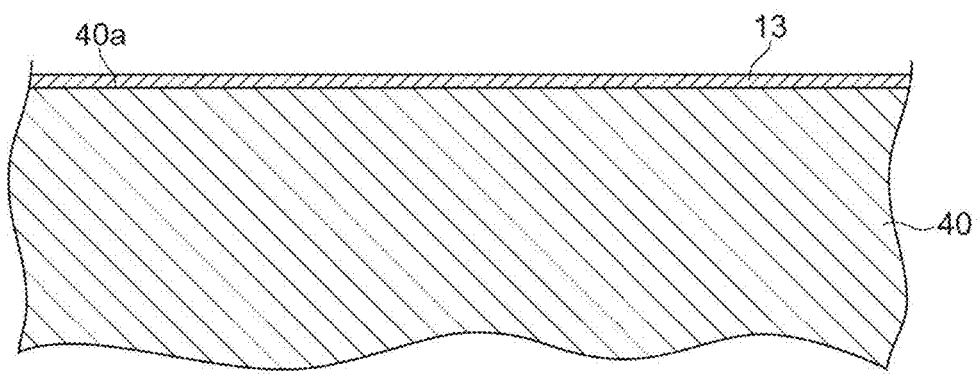
(c)
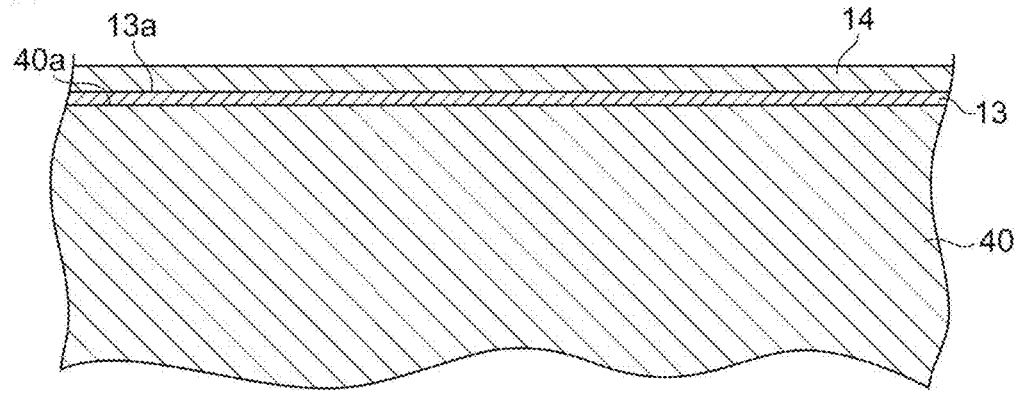

Fig.14
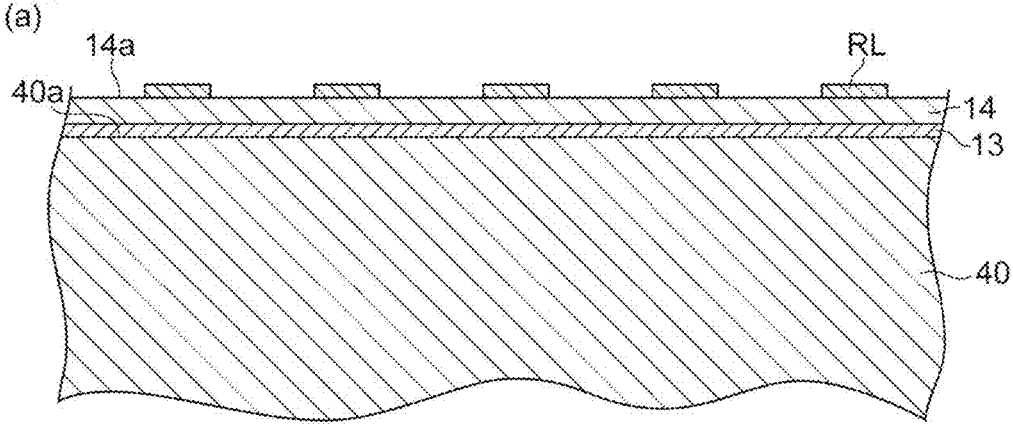
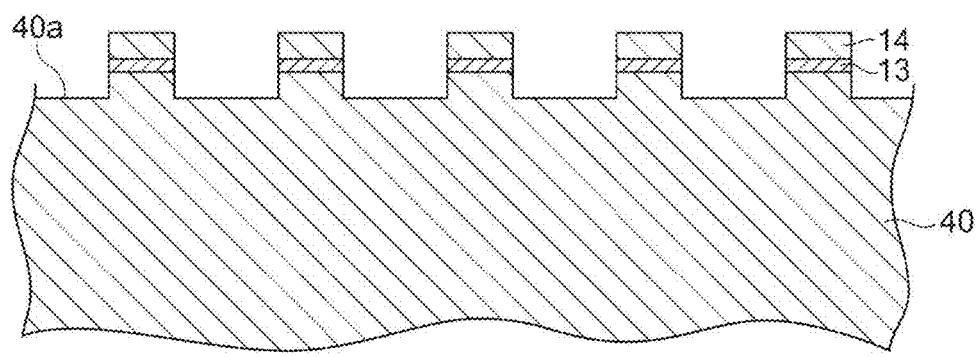
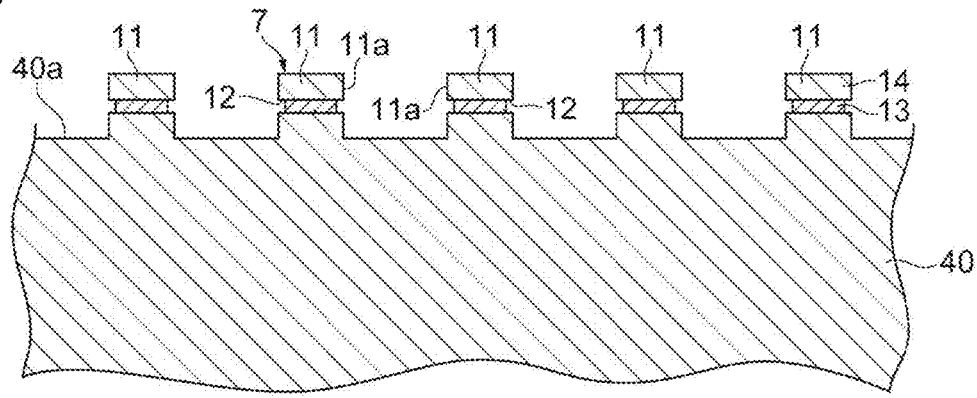

SURFACE-ENHANCED RAMAN SCATTERING ELEMENT AND METHOD FOR MANUFACTURING SAME

TECHNICAL FIELD

The present invention relates to a surface-enhanced Raman scattering element and a method of manufacturing the same.

BACKGROUND ART

As a surface-enhanced Raman scattering element of the related art, a surface-enhanced Raman scattering element including a fine metal structure that causes surface-enhanced Raman scattering (SERS) is known (see, for example, Patent Literature 1 and Non-Patent Literature 1). In such a surface-enhanced Raman scattering element, if a sample that is a target of Raman spectroscopic analysis is brought into contact with the fine metal structure and is irradiated with excitation light in this state, surface-enhanced Raman scattering occurs, and Raman scattered light enhanced, for example, about $10^8$ times is emitted.

By the way, for example, Patent Literature 2 describes a fine metal structure in which a metal layer is formed to be in a non-contact state (so that an interval from a shortest portion is about 5 nm to 10 μm) on each of one surface of a substrate and an upper surface of a plurality of microprojections formed on the one surface of the substrate (or a bottom surface of a plurality of micropores formed in the one surface of the substrate).

CITATION LIST

Patent Literature

[Patent Literature 1] Japanese Unexamined Patent Publication No. 2011-33518
[Patent Literature 2] Japanese Unexamined Patent Publication No. 2009-222507

Non Patent Literature

Non-Patent Literature 1: "Q-SERS™ G1 Substrate", [online], Opto Science Inc., [Search on Jul. 19, 2012], Internet <URL: http://www.optoscience.com/maker/nanova/pdf/Q-SERS_G1.pdf>

SUMMARY OF INVENTION

Technical Problem

As described above, if a so-called nanogap is formed in a fine metal structure, local electrical field enhancement occurs when excitation light is irradiated, and the intensity of surface-enhanced Raman scattering is increased.

Accordingly, an object of the present invention is to provide a surface-enhanced Raman scattering element capable of increasing the intensity of surface-enhanced Raman scattering using preferable nanogaps, and a method of manufacturing the same.

Solution to Problem

A surface-enhanced Raman scattering element of one aspect of the present invention comprises: a substrate; a fine structure portion formed on a surface of the substrate and having a plurality of projections; and a conductor layer formed on the fine structure portion and constituting an optical functional portion that causes surface-enhanced Raman scattering, wherein a recessed region is provided in an outer surface of each of the plurality of projections, and a plurality of gaps are formed in the conductor layer by forming the conductor layer on the outer surface of each of the plurality of projections in a state in which at least a portion of an inner surface of the recessed region is exposed.

In this surface-enhanced Raman scattering element, the conductor layer is formed on the outer surface of each of the plurality of projections in a state in which at least a portion of the inner surface of the recessed region is exposed, and accordingly, a plurality of gaps are formed in the conductor layer constituting the optical functional portion. The gap formed in this conductor layer preferably functions as a nanogap in which local electrical field enhancement occurs. Therefore, according to the surface-enhanced Raman scattering element, it is possible to increase the intensity of the surface-enhanced Raman scattering using the preferable nanogaps.

In a surface-enhanced Raman scattering element of one aspect of the present invention, the plurality of projections may be periodically arranged along the surface. According to this configuration, it is possible to stably increase the intensity of surface-enhanced Raman scattering.

In a surface-enhanced Raman scattering element of one aspect of the present invention, a plurality of recessed regions may be provided for one of the projections. According to this configuration, it is possible to increase the number of gaps preferably functioning as nanogaps.

In a surface-enhanced Raman scattering element of one aspect of the present invention, the recessed region may be a groove extending along a center line of the projection or the recessed region may be a groove extending to surround a center line of the projection. In any of the configurations, it is possible to cause the gaps formed in positions corresponding to the recessed regions to preferably function as nanogaps.

A surface-enhanced Raman scattering element of one aspect of the present invention comprises: a substrate; a fine structure portion formed on a surface of the substrate and having a plurality of depressions; and a conductor layer formed on the fine structure portion and constituting an optical functional portion that causes surface-enhanced Raman scattering, wherein a recessed region is provided in an inner surface of each of the plurality of depressions, and a plurality of gaps are formed in the conductor layer by forming the conductor layer on the inner surface of each of the plurality of depressions in a state in which at least a portion of an inner surface of the recessed region is exposed.

In this surface-enhanced Raman scattering element, the conductor layer is formed on the inner surface of each of the plurality of depressions in a state in which at least a portion of the inner surface of the recessed region is exposed, and accordingly, a plurality of gaps are formed in the conductor layer constituting the optical functional portion. The gap formed in this conductor layer preferably functions as a nanogap in which local electrical field enhancement occurs. Therefore, according to the surface-enhanced Raman scattering element, it is possible to increase the intensity of the surface-enhanced Raman scattering using the preferable nanogaps.

In a surface-enhanced Raman scattering element of one aspect of the present invention, the plurality of depressions are periodically arranged along the surface. According to this configuration, it is possible to stably increase the intensity of surface-enhanced Raman scattering.

In the surface-enhanced Raman scattering element of one aspect of the present invention, a plurality of recessed regions are provided for one of the depressions. According to this configuration, it is possible to increase the number of gaps preferably functioning as nanogaps.

In the surface-enhanced Raman scattering element of one aspect of the present invention, the recessed region may be a groove extending along a center line of the depression or the recessed region may be a groove extending to surround a center line of the depression. In any of the configurations, it is possible to cause the gaps formed in positions corresponding to the recessed regions to preferably function as nanogaps.

A method of manufacturing a surface-enhanced Raman scattering element of one aspect of the present invention comprises a first step of forming a fine structure portion having a plurality of projections on a surface of a substrate, a recessed region being provided in an outer surface of each of the plurality of projections; and a second step of forming a conductor layer to constitute an optical functional portion causing surface-enhanced Raman scattering on the fine structure portion using vapor phase growth, wherein the second step includes stopping the vapor phase growth in a state in which at least a portion of an inner surface of the recessed region is exposed.

In this method of manufacturing a surface-enhanced Raman scattering element, the vapor phase growth for forming the conductor layer on the fine structure portion is stopped in a state in which at least a portion of the inner surface of the recessed region is exposed. Accordingly, it is easy for the gaps preferably functioning as nanogaps in which local electrical field enhancement occurs to be formed in portions corresponding to the recessed regions and base end portions of the projections in the conductor layer. Therefore, according to the method of manufacturing the surface-enhanced Raman scattering element, it is possible to obtain a surface-enhanced Raman scattering element capable of increasing the intensity of the surface-enhanced Raman scattering using the preferable nanogaps.

A method of manufacturing a surface-enhanced Raman scattering element of one aspect of the present invention comprises: a first step of forming a fine structure portion having a plurality of depressions on a surface of a substrate, a recessed region being provided in an inner surface of each of the plurality of depressions; and a second step of forming a conductor layer to constitute an optical functional portion causing surface-enhanced Raman scattering on the fine structure portion using vapor phase growth, wherein the second step includes stopping the vapor phase growth in a state in which at least a portion of an inner surface of the recessed region is exposed.

In this method of manufacturing a surface-enhanced Raman scattering element, the vapor phase growth for forming the conductor layer on the fine structure portion is stopped in a state in which at least a portion of the inner surface of the recessed region is exposed. Accordingly, it is easy for the gaps preferably functioning as nanogaps in which local electrical field enhancement occurs to be formed in portions corresponding to the recessed regions and bottom portions of the depressions in the conductor layer. Therefore, according to the method of manufacturing the surface-enhanced Raman scattering element, it is possible to obtain a surface-enhanced Raman scattering element capable of increasing the intensity of the surface-enhanced Raman scattering using the preferable nanogaps.

In a method of manufacturing the surface-enhanced Raman scattering element of one aspect of the present invention, the vapor phase growth may be vapor deposition. Since the vapor deposition is vapor phase growth with excellent anisotropy, it is possible to inhibit the conductor layer from entering the recessed region and to form the gaps preferably functioning as nanogaps in which local electrical field enhancement occurs, in a portion corresponding to the recessed region in the conductor layer.

Advantageous Effects of Invention

According to the present invention, it is possible to provide a surface-enhanced Raman scattering element capable of increasing the intensity of surface-enhanced Raman scattering using preferable nanogaps, and a method of manufacturing the same.

BRIEF DESCRIPTION OF DRAWINGS

FIG. 6 is a cross-sectional view illustrating a process of manufacturing the surface-enhanced Raman scattering element of FIG. 3.

FIG. 7 is a cross-sectional view illustrating a process of manufacturing the surface-enhanced Raman scattering element of FIG. 3.

FIG. 9 is an SEM photograph of an optical functional portion of a surface-enhanced Raman scattering element.

FIG. 13 is a cross-sectional view illustrating a process of manufacturing the surface-enhanced Raman scattering element of FIG. 11.

FIG. 14 is a cross-sectional view illustrating a process of manufacturing the surface-enhanced Raman scattering element of FIG. 11.

DESCRIPTION OF EMBODIMENTS

Hereinafter, preferred embodiments of the present invention will be described in detail with reference to the drawings. In each figure, the same or corresponding portions are denoted with the same reference signs, and repeated description will be omitted.

First Embodiment

Figure 1:
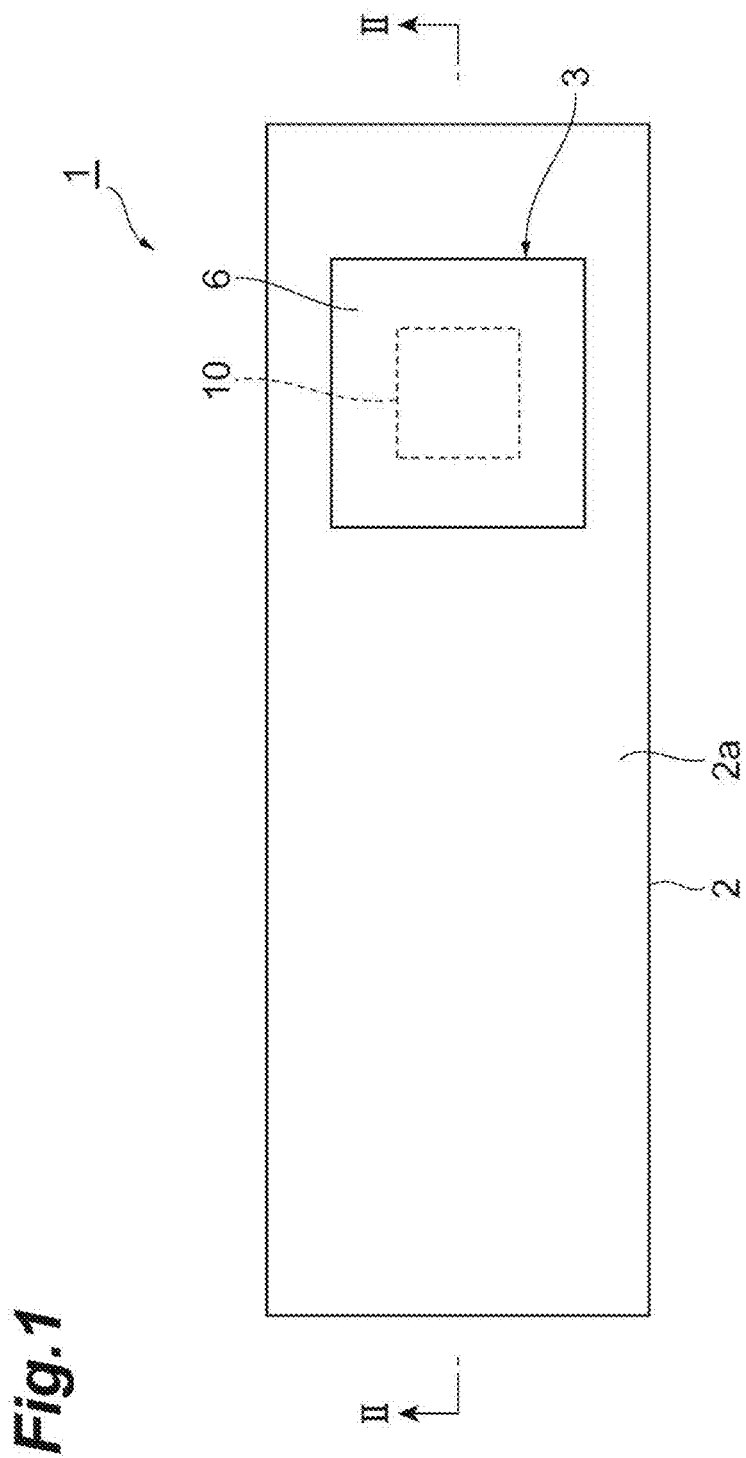
FIG. 1 is a plan view of a surface-enhanced Raman scattering unit including a surface-enhanced Raman scattering element according to a first embodiment of the present invention.
Figure 2:
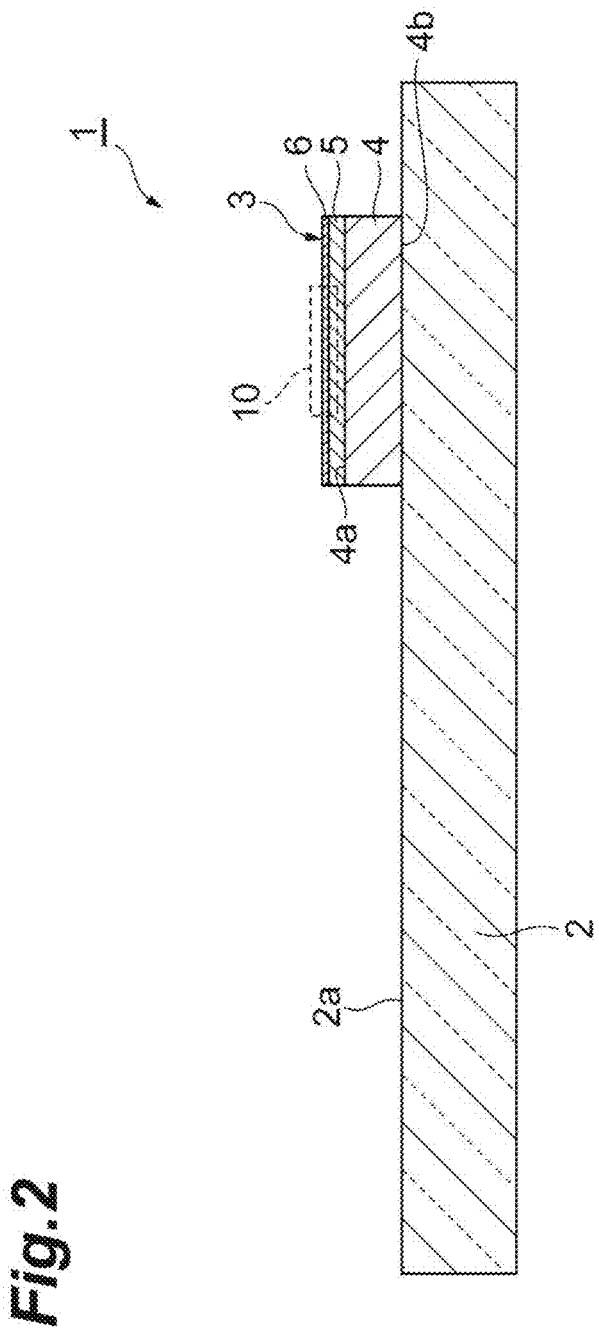
FIG. 2 is a cross-sectional view of the surface-enhanced Raman scattering unit taken along line II-II of FIG. 1.

As illustrated in FIGS. 1 and 2, a SERS unit (surface-enhanced Raman scattering unit) 1 of a first embodiment includes a handling substrate 2, and a SERS element (surface-enhanced Raman scattering element) 3 attached to the handling substrate 2. The handling substrate 2 is, for example, a rectangular plate-shaped slide glass, resin substrate, or ceramic substrate. The SERS element 3 is arranged on a surface 2a of the handling substrate 2 in a state of being offset toward one end portion in a longitudinal direction of the handling substrate 2.

The SERS element 3 includes a substrate 4 mounted on the handling substrate 2, a molded layer 5 formed on the substrate 4, and a conductor layer 6 formed on the molded layer 5. The substrate 4 is formed of silicon, glass, or the like in a rectangular plate shape, and has an appearance with a size of hundreds of μm×hundreds of μm to tens of mm×tens of mm and a thickness of about 100 μm to 2 mm. A back surface 4b of the substrate 4 is bonded to the surface 2a of the handling substrate 2 by direct bonding, bonding using a metal such as solder, eutectic bonding, fusion bonding using laser light irradiation or the like, anodic bonding, or bonding using a resin.

Figure 3:
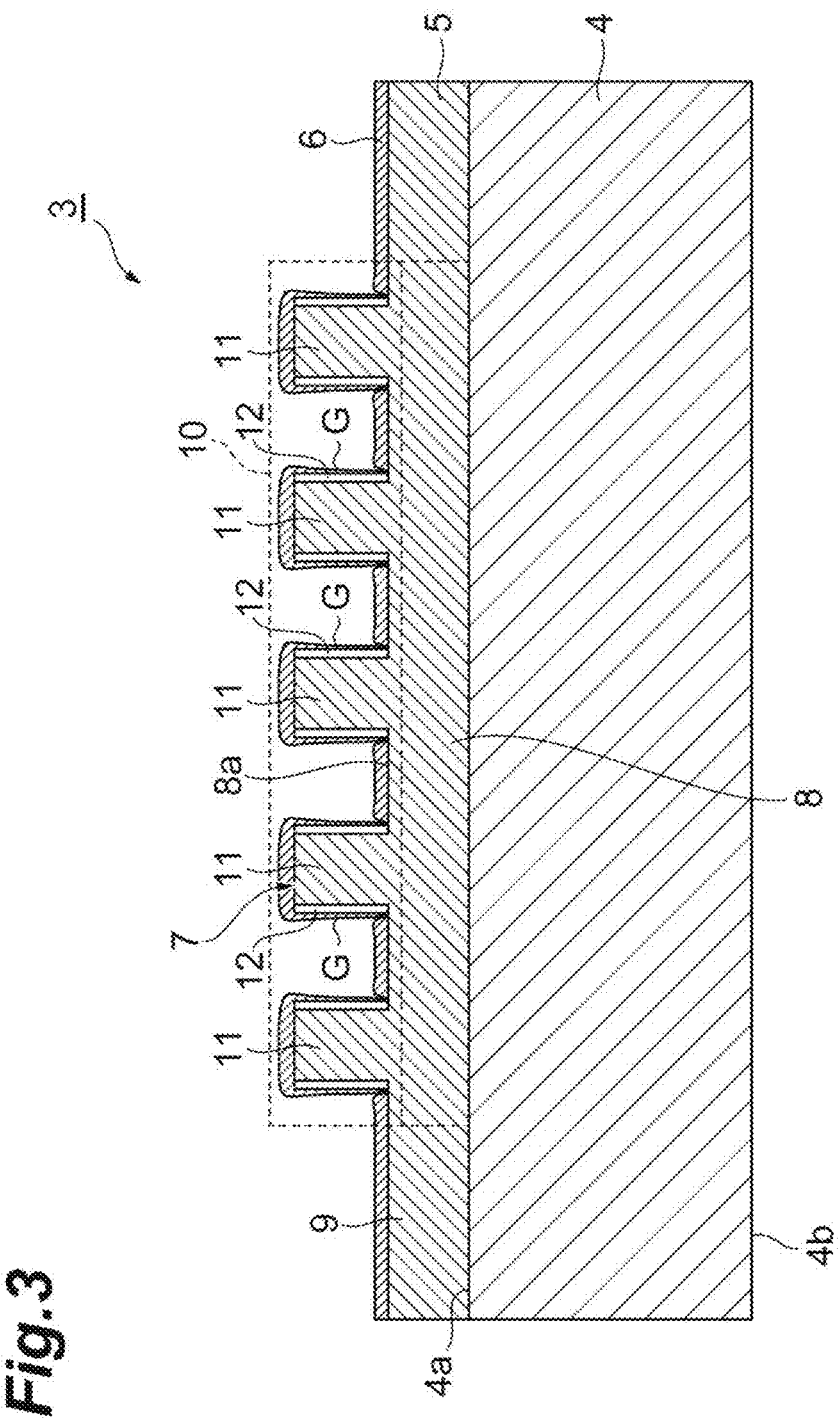
FIG. 3 is a cross-sectional view of the surface-enhanced Raman scattering element of FIG. 2.

As illustrated in FIG. 3, the molded layer 5 includes a fine structure portion 7, a support portion 8, and a frame portion 9. The fine structure portion 7 is a region having a periodic pattern and is formed on a surface layer opposite to the substrate 4 at a center portion of the molded layer 5. In the fine structure portion 7, a plurality of columnar pillars (projections) 11 having a diameter and a height of several nm to hundreds of nm are arranged periodically at a pitch of tens of nm to hundreds of nm (preferably, 250 nm to 800 nm) along the surface 4a of the substrate 4. When viewed from a thickness direction of the substrate 4, the fine structure portion 7 has a rectangular appearance having a size of hundreds of m×hundreds of μm to tens of mm×tens of mm. The support portion 8 is a rectangular region that supports the fine structure portion 7 and is formed on the surface 4a of the substrate 4. The frame portion 9 is a rectangular annular region surrounding the support portion 8 and is formed on the surface 4a of the substrate 4. The support portion 8 and the frame portion 9 have a thickness of about tens of nm to tens of μm. Such a molded layer 5 is integrally formed, for example, by molding a resin (acrylic type, fluorine type, epoxy type, silicone type, urethane type, PET, polycarbonate, inorganic/organic hybrid material or the like) or low melting point glass arranged on the substrate 4 using a nanoimprinting method.

The conductor layer 6 is formed from the fine structure portion 7 to the frame portion 9. In the fine structure portion 7, the conductor layer 6 reaches a surface 8a of the support portion 8 exposed on the side opposite to the substrate 4. The conductor layer 6 has a thickness of several nm to several μm. Such a conductor layer 6 is formed, for example, by vapor-depositing a conductor such as metal (Au, Ag, Al, Cu, Pt, or the like) on the molded layer 5 formed using the nanoimprinting method. In the SERS element 3, the conductor layer 6 formed on the fine structure portion 7 and the surface 8a of the support portion 8 constitutes an optical functional portion 10 that causes surface-enhanced Raman scattering.

Figure 4:
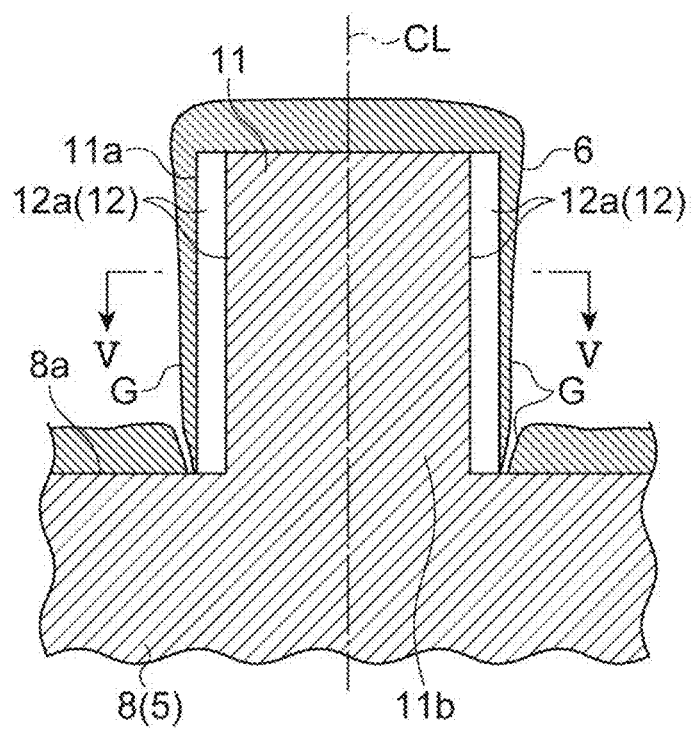
FIG. 4 is a cross-sectional view of a pillar and a conductor layer of FIG. 3.
Figure 5:
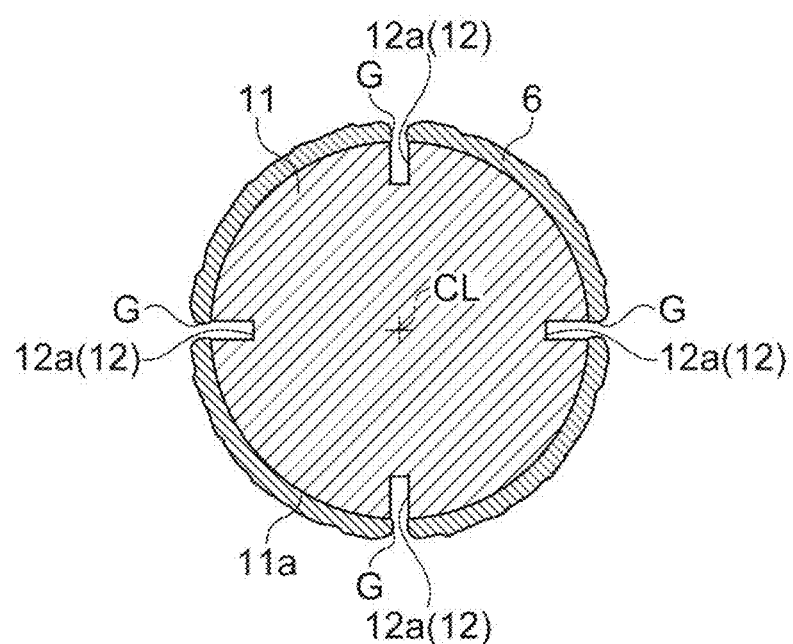
FIG. 5 is a cross-sectional view of the pillar and the conductor layer taken along line V-V in FIG. 4.

As illustrated in FIGS. 4 and 5, grooves (recessed regions) 12 having a rectangular cross section are provided on a side surface (outer surface) 11a of each pillar 11. The grooves 12 extend along a center line CL of the pillar 11, and a plurality of grooves 12 (four grooves every 90° with respect to the center line CL in the SERS element 3 of the first embodiment) are provided for one pillar 11. The groove 12 has a width and a depth of several nm to tens of nm. The conductor layer 6 is formed on the surface 8a of the support portion 8 and an outer surface of each pillar 11. The conductor layer 6 does not cover an entire inner surface 12a of the groove 12 and does not completely cover an opening of the groove 12. That is, at least a portion of the inner surface 12a of the groove 12 is exposed to the outside of the groove 12. In the conductor layer 6, the conductor layer 6 is formed on the side surface 11a of each pillar 11 in a state in which at least a portion of the inner surface 12a of each groove 12 is exposed, and accordingly, a plurality of gaps G are formed. That is, in the conductor layer 6 constituting the optical functional portion 10, the conductor layer 6 along the side surface 11a of the pillar 11 is separated by the groove 12, and the gap G is formed along each groove 12. The gap G has an interval of about 0 to tens of nm. The center line CL of the pillar 11 is a line passing through a centroid of each cross-sectional shape of the pillar 11 perpendicular to the center line CL.

The SERS unit 1 configured as described above is used as follows. First, an annular spacer made of, for example, silicone or the like is arranged on the surface 2a of the handling substrate 2 to surround the SERS element 3. Subsequently, a sample as a solution (or a sample in which a powder sample is dispersed in a solution such as water or ethanol) is dropped into the spacer using a pipette or the like, and the sample is placed on the optical functional portion 10. Subsequently, in order to reduce a lens effect, a cover glass is placed on the spacer and brought into close contact with the solution sample.

Subsequently, the SERS unit 1 is set in a Raman spectroscopic analysis device, and the sample arranged on the optical functional portion 10 is irradiated with excitation light through the cover glass. Thus, surface-enhanced Raman scattering occurs at an interface between the optical functional portion 10 and the sample, and Raman scattered light derived from the sample is enhanced, for example, about $10^8$ times and emitted. Therefore, in the Raman spectroscopic analysis device, highly accurate Raman spectroscopic analysis can be achieved.

A method of arranging the sample on the optical functional portion 10 includes the following method, in addition to the above-described method. For example, the handling substrate 2 may be gripped, and the SERS element 3 may be immersed in a sample as a solution (or a sample in which a powder sample is dispersed in a solution such as water or ethanol), pulled up, and blown to dry the sample. Further, a small amount of sample as a solution (or the sample in which a powder sample is dispersed in a solution such as water or ethanol) may be dropped onto the optical functional portion 10, and the sample may be naturally dried. Further, a sample as a powder may be directly dispersed on the optical functional portion 10.

As described above, in the SERS element 3 of the first embodiment, the conductor layer 6 is formed on the side surface 11a of each pillar 11 in a state in which at least a portion of the inner surface 12a of the groove 12 is exposed, and accordingly, the plurality of gaps G are formed in the conductor layer 6 constituting the optical functional portion 10. The gap G formed in the conductor layer 6 preferably functions as a nanogap in which local enhancement of an electrical field occurs (hereinafter simply referred to as "nanogap"). Therefore, according to the SERS element 3 of the first embodiment, it is possible to increase the intensity of the surface-enhanced Raman scattering using the preferable nanogaps.

Further, since the plurality of pillars 11 are periodically arranged along the surface 4a of the substrate 4, it is possible to stably increase the intensity of the surface-enhanced Raman scattering.

Further, since a plurality of grooves 12 are provided for one pillar 11, it is possible to increase the number of gaps G preferably functioning as nanogaps.

Next, a method of manufacturing the SERS element 3 of the first embodiment will be described. First, as illustrated in FIG. 6(a), a master mold MM and a film base material F are prepared. The master mold MM includes fine structure portions M7 corresponding to the fine structure portion 7, and a support portion M8 that supports the fine structure portions M7. A plurality of fine structure portions M7 are arranged in a matrix form on the support portion M8. Subsequently, as illustrated in FIG. 6(b), the film base material F is pressed against the master mold MM, and is pressurized and heated in this state, such that a pattern of the plurality of fine structure portions M7 is transferred to the film base material F. Subsequently, as illustrated in FIG. 6(c), by releasing the film base material F from the master mold MM, a replica mold (replica film) RM to which the pattern of the plurality of fine structure portions M has been transferred is obtained. The replica mold RM may be formed by coating the film base material F with a resin (for example, an epoxy resin, an acrylic resin, a fluorine resin, a silicone resin, an urethane resin, or an organic/inorganic hybrid resin). In a case in which the resin to be applied on the film base material F has UV curability, the replica mold R (UV nanoimprint) can be obtained by curing the resin coated on the film base material F through UV irradiation instead of heat nanoimprinting.

Subsequently, as illustrated in FIG. 7(a), a silicon wafer 40 as the substrate 4 is prepared and a surface 40a thereof is coated with a UV curable resin to thereby form a nanoimprint layer 50 as the molded layer 5 on the silicon wafer 40. Subsequently, as illustrated in FIG. 7(b), the replica mold RM is pressed against the nanoimprint layer 50, which is irradiated with UV in this state to cure the nanoimprint layer 50. Accordingly, the pattern of the replica mold RM is transferred to the nanoimprint layer 50. Subsequently, as illustrated in FIG. 7(c), by releasing the replica mold RM from the nanoimprint layer 50, the silicon wafer 40 on which a plurality of fine structure portions 7 are formed is obtained. Heat curing may be performed to ensure curing of the resin.

This step is a first step of forming, on the surface 4a of the substrate 4, the fine structure portions 7 having the plurality of pillars 11 in which the plurality of grooves 12 are provided in the respective side surfaces 11a.

Subsequently, a metal such as Au or Ag is deposited on the molded layer 5 to form a conductor layer 6 using a vapor deposition method such as resistive heating evaporation or electron beam evaporation. In this case, a plurality of gaps G are formed in the conductor layer 6 constituting the optical functional portion 10. This step is a second step of forming the conductor layer 6 constituting the optical functional portion 10 that causes surface-enhanced Raman scattering, on the fine structure portion 7 using vapor phase growth. In the second step, the vapor phase growth is stopped in a state in which at least a portion of the inner surface 12a of each groove 12 is exposed, before the entire inner surface 12a of each groove 12 is covered with the conductor layer 6.

Subsequently, the silicon wafer 40 is cut for each fine structure portion 7 (in other words, for each optical functional portion 10) to obtain a plurality of SERS elements 3. In order to obtain the SERS unit 1, the SERS elements 3 manufactured as described above may be attached on the handling substrate 2.

As described above, in the method of manufacturing the SERS element 3 of the first embodiment, the vapor phase growth for forming the conductor layer 6 on the fine structure portion 7 is stopped in a state in which at least a portion of the inner surface 12a of each groove 12 is exposed before the conductor layer 6 covers the entire inner surface 12a of each groove 12. Accordingly, it is difficult for the opening of the groove 12 to be blocked by the conductor layer 6, and it is easy for the gap G preferably functioning as a nanogap to be formed in the portion corresponding to the groove 12 in the conductor layer 6, as illustrated in FIG. 4. In this case, since a thickness of the conductor layer 6 is small, it is easy for a desired gap G according to a shape of the groove 12 to be formed. Further, it is easy for the gap G preferably functioning as a nanogap to be formed in a portion corresponding to a base end portion 11b of the pillar 11 (a corner portion between the side surface 11a of the pillar 11 and the surface 8a of the support portion 8) in the conductor layer 6. That is, in the portion corresponding to the base end portion 11b of the pillar 11, the gap G which opens on the opposite side of the substrate 4 is formed to surround each pillar 11 when viewed from a direction in which the pillar 11 projects (that is, a thickness direction of the substrate 4) by the conductor layer 6 along the side surface 11a of the pillar 11 and the conductor layer 6 along the surface 8a of the support portion 8. In a deepest portion of the gap G, the conductor layer 6 along the side surface 11a of the pillar 11 and the conductor layer 6 along the surface 8a of the support portion 8 may be connected or may be separated (the surface 8a of the support portion 8 may be exposed in the deepest portion of the gap G). For example, in the portion corresponding to the base end portion 11b of the pillar 11, the gap G is formed in a groove shape which extends annularly to surround each pillar 11 when viewed from a direction in which the pillar 11 projects. As described above, according to the method of manufacturing the SERS element 3 of the first embodiment, it is possible to obtain the SERS element 3 in which the intensity of surface-enhanced Raman scattering can be increased using the preferable nanogaps.

Figure 8:
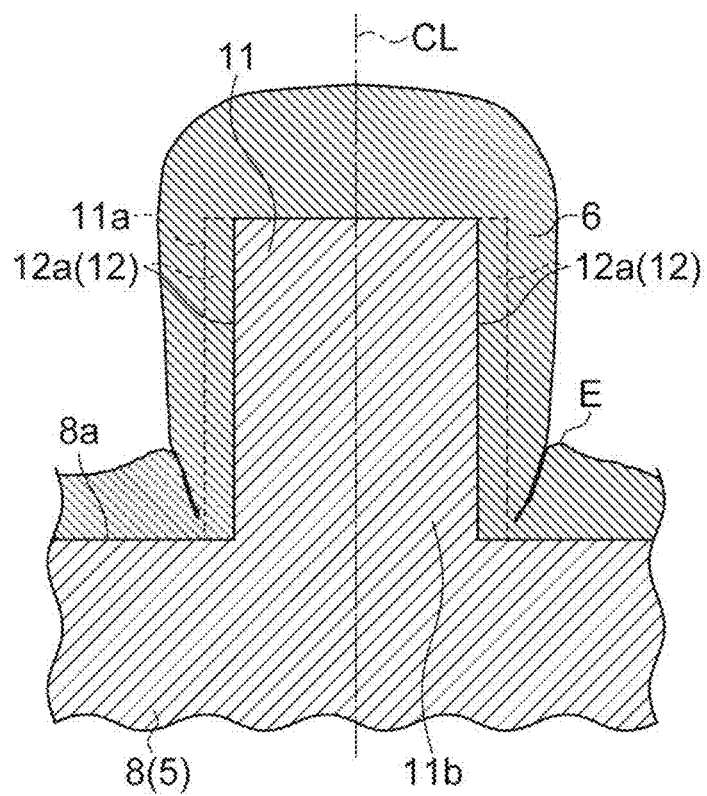
FIG. 8 is a cross-sectional view of a pillar and a conductor layer of a surface-enhanced Raman scattering element of a comparative example.

If vapor phase growth for forming the conductor layer 6 on the fine structure portion 7 is continued until the conductor layer 6 covers the entire inner surface 12a of each groove 12, a raised portion E (a portion raised by depositing a large amount of conductor in a portion in which the conductor layer 6 along the side surface 11a of the pillar 11 and the conductor layer 6 along the surface 8a of the support portion 8 meet) is formed in a portion corresponding to the base end portion 11b of the pillar 11 in the conductor layer 6 as illustrated in FIG. 8, and it is difficult for the gap G preferably functioning as the nanogap to be formed. FIG. 9(a) illustrates an SEM photograph of the optical functional portion 10 in a case in which the gap G preferably functioning as a nanogap is formed in the portion corresponding to each of the groove 12 and the base end portion 11b of the pillar 11 in the conductor layer 6 (Example). FIG. 9(b) illustrates an SEM photograph of the optical functional portion 10 in a case in which the raised portion E is formed in the portion corresponding to the base end portion 11b of the pillar 11 in the conductor layer 6 (Comparative example).

Further, since vapor deposition that is vapor phase growth with excellent anisotropy (high anisotropy) is performed as the vapor phase growth for forming the conductor layer 6 on the fine structure portion 7, it is possible to inhibit the conductor layer 6 from entering each groove 12 and form the gap G preferably functioning as a nanogap in the portion corresponding to the groove 12 in the conductor layer 6. Further, in a vapor deposition method that is a vapor phase growth method with excellent anisotropy, if conductor particles (conductive particles) are deposited from the direction in which the pillar 11 projects, it is easy for the conductive particles to be adhered on the surface 8a of the support portion 8 and in the vicinity of a distal end (near the top) of the pillar 11, whereas it is difficult for the conductive particles to reach a base of the pillar 11 (a portion corresponding to the base end portion 11b of the pillar 11) due to a shadowing effect by the conductive particles adhered in the vicinity of the distal end of the pillar 11. Therefore, it is possible to inhibit the raised portion E from being formed in the portion corresponding to the base end portion 11b of the pillar 11 and to form the gap G preferably functioning as a nanogap.

Further, by only transferring the pattern having a two-dimensional shape of the replica mold RM, it is possible to form the groove 12 extending along the center line CL of the pillar 11 on the side surface 11a of the pillar 11. Since it is easy to change a design of the pattern having a two-dimensional shape in the replica mold RM, the SERS element 3 in which preferable nanogaps have been formed can be manufactured with good yield.

As the nanoimprinting method, thermal nanoimprinting can also be used, in addition to the UV nanoimprinting described above. In the case of thermal nanoimprinting, nickel, silicon, and the like can be used as a molding material.

Further, in place of the above-described nanoimprinting method, a mask with the pattern having a two-dimensional shape may be formed using photo etching, electron beam depiction, or the like, and the fine structure portion 7 may be formed on the substrate 4 by etching using the mask. In this case, since it is easy to change a design of the pattern having a two-dimensional shape in the mask, the SERS element 3 in which preferable nanogaps have been formed can be manufactured with good yield.

Figure 10:
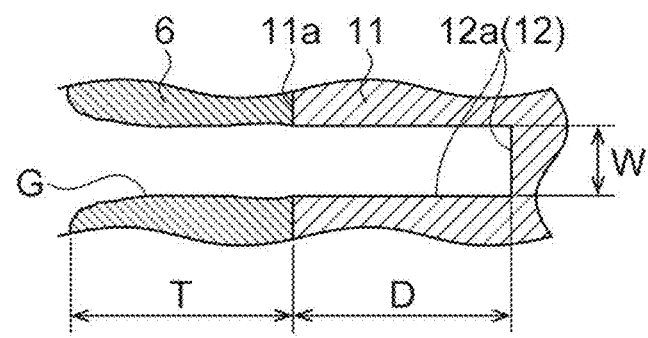
FIG. 10 is a cross-sectional view of a portion of the pillar and the conductor layer of FIG. 5.

Next, examples of dimensions will be described. As described above, when the plurality of pillars 11 having a columnar shape having a diameter and a height of several nm to hundreds of nm are periodically arranged at a pitch of tens of nm to hundreds of nm (preferably, 250 nm to 800 nm) along the surface 4a of the substrate 4 in the fine structure portion 7, the groove 12 has a width and depth of several nm to tens of nm, and the conductor layer 6 has a thickness of several nm to several μm. In this case, the gap G has an interval of about 0 to tens of nm. However, it is preferable that a width W of the groove 12 is set as a width corresponding to about 1/200 to about 1 of the thickness of the conductor layer 6, and a depth D of the groove 12 is set to about 1 nm to hundreds of nm (a depth corresponding to less than a half of the diameter of the pillar 11), as illustrated in FIG. 10, in consideration of the gap G preferably functioning as a nanogap being formed in the portion corresponding to each of the groove 12 and the base end portion 11b of the pillar 11 in the conductor layer 6 as illustrated in FIG. 4. It is preferable for the thickness T of the conductor layer 6 to be several nm to hundreds of rm. Accordingly, the gaps G having intervals of several Å to tens of nm are formed in the portion corresponding to each of the groove 12 and the base end portion 11b of the pillar 11 in the conductor layer 6.

Second Embodiment

Figure 11:
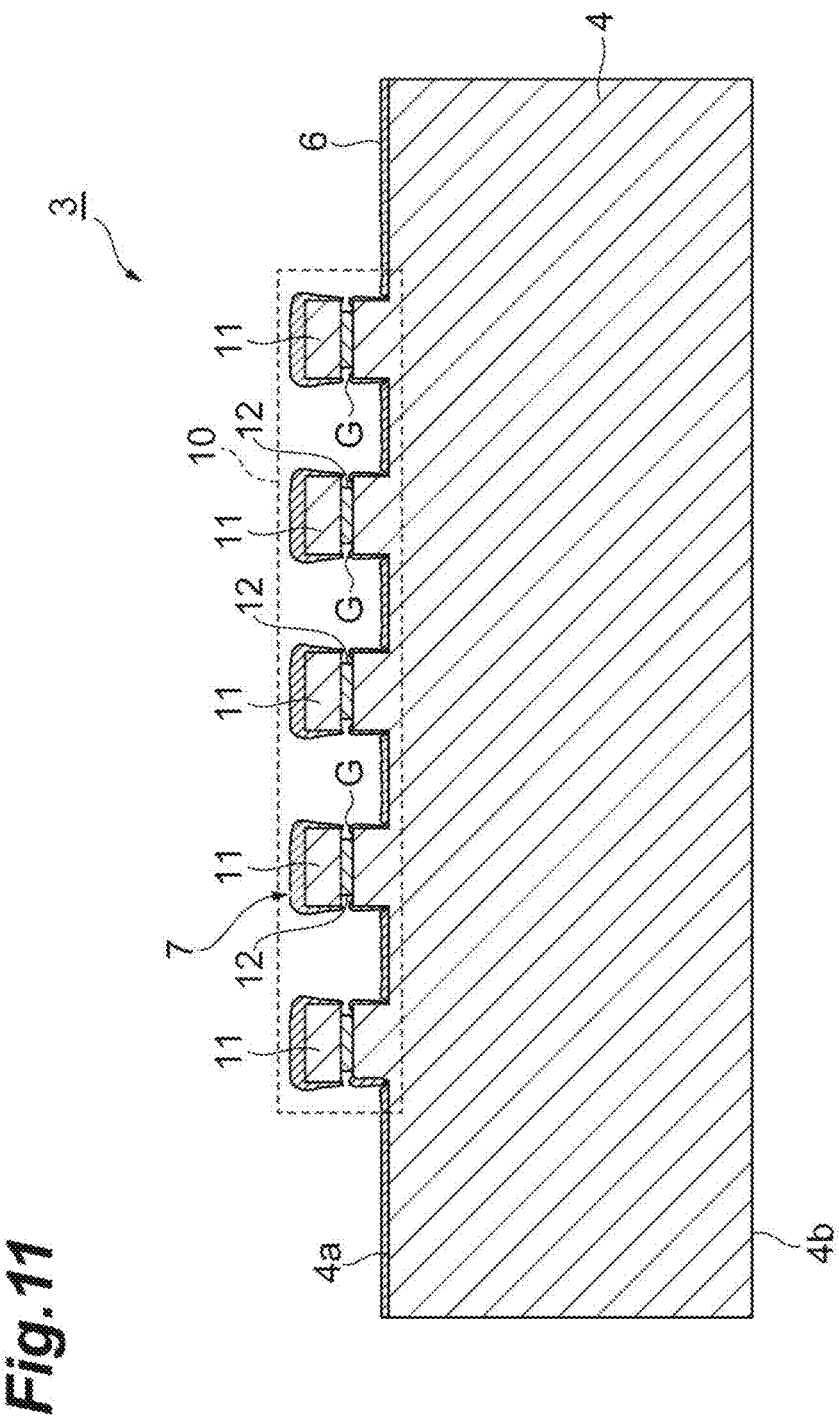
FIG. 11 is a cross-sectional view of a surface-enhanced Raman scattering element according to a second embodiment of the present invention.
Figure 12:
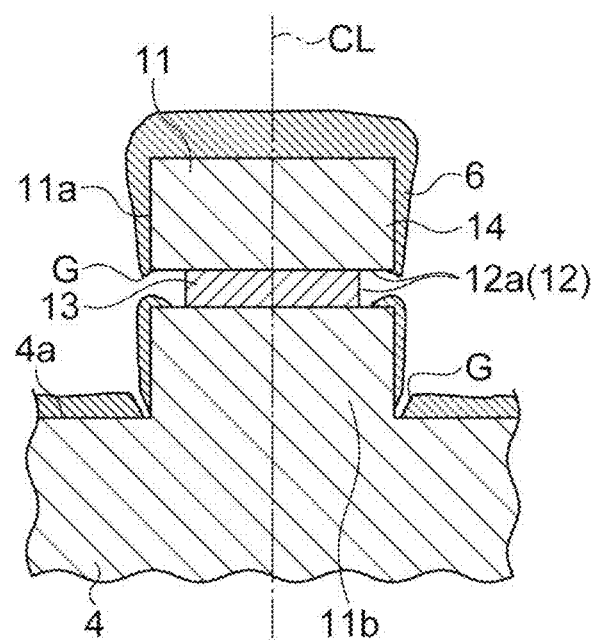
FIG. 12 is a cross-sectional view of the pillar and the conductor layer of FIG. 11.

As illustrated in FIG. 11, an SERS element 3 of a second embodiment primarily differs from the SERS element 3 of the first embodiment described above in that a fine structure portion 7 is formed on a surface 4a of a substrate 4, and a groove 12 extends to surround a center line CL of a pillar 11 (see FIG. 12). In the SERS element 3 of the second embodiment, the fine structure portion 7 is formed in a central portion of the surface 4a of the substrate 4, and has an appearance having a rectangular shape of hundreds of μm×hundreds of μm to tens of mm×tens of mm when viewed from a thickness direction of the substrate 4. Pillars 11 of the fine structure portion 7 are periodically arranged at a pitch of tens of nm to hundreds of nm (preferably, 250 nm to 800 nm) along the surface 4a of the substrate 4.

A conductor layer 6 is formed from the fine structure portion 7 to the surface 4a of the substrate 4. The conductor layer 6 reaches the surface 4a of the substrate 4 exposed at the fine structure portion 7. In the SERS element 3, an optical functional portion 10 that causes surface-enhanced Raman scattering is constituted by the conductor layer 6 formed on the fine structure portion 7 and the surface 4a of the substrate 4 exposed at the fine structure portion 7.

As illustrated in FIG. 12, the groove 12 extends annularly to surround the center line CL of the pillar 11, and one groove is provided for one pillar 11. The conductor layer 6 is formed on the surface 4a of the substrate 4 and the outer surface of each pillar 11. The conductor layer 6 does not cover an entire inner surface 12a of the groove 12 and does not completely cover an opening of the groove 12. That is, at least a portion of the inner surface 12a of the groove 12 is exposed to the outside of the groove 12. In the conductor layer 6, the conductor layer 6 is formed on the side surface 11a of each pillar 11 in a state in which at least a portion of the inner surface 12a of each groove 12 is exposed, and accordingly, a plurality of gaps G are formed. That is, in the conductor layer 6 constituting the optical functional portion 10, the conductor layer 6 along the side surface 11a of the pillar 11 is separated by the groove 12, and the gap G is formed along each groove 12.

As described above, in the SERS element 3 of the second embodiment, the conductor layer 6 is formed on the side surface 11a of each pillar 11 in a state in which at least a portion of the inner surface 12a of the groove 12 is exposed, and accordingly, the plurality of gaps G are formed in the conductor layer 6 constituting the optical functional portion 10. The gap G formed in the conductor layer 6 preferably functions as a nanogap. Therefore, according to the SERS element 3 of the second embodiment, it is possible to increase the intensity of the surface-enhanced Raman scattering using the preferable nanogaps.

Further, since the plurality of pillars 11 are periodically arranged along the surface 4a of the substrate 4, it is possible to stably increase the intensity of the surface-enhanced Raman scattering.

Next, a method of manufacturing the SERS element 3 of the second embodiment will be described. First, as illustrated in FIG. 13(a), a silicon wafer 40 serving as a substrate 4 is prepared. Subsequently, as illustrated in FIG. 13(b), a sacrificial layer 13 made of $SiO_2$ is formed on a surface 40a of the silicon wafer 40. Subsequently, as illustrated in FIG. 13(c), a surface layer 14 made of polysilicon is formed on a surface 13a of the sacrificial layer 13.

Subsequently, as illustrated in FIG. 14(a), a resist layer RL is formed on a surface 14a of the surface layer 14. The resist layer RL has a pattern formed by photo etching, electron beam lithography, nanoimprint lithography, or the like. The pattern of the resist layer RL corresponds to a plurality of fine structure portions 7, and a portion corresponding to the pillar 11 is masked for each fine structure portion 7. Subsequently, as illustrated in FIG. 14(b), the surface layer 14 of a region not masked with the resist layer RL, the sacrificial layer 13, and a surface layer of the silicon wafer 40 are removed by dry etching using the resist layer RL as a mask, and then, the remaining resist layer RL is removed. Subsequently, as illustrated in FIG. 14(c), a surface layer of the sacrificial layer 13 exposed to the side is selectively removed by dry etching or wet etching using another etchant, and the groove 12 is formed in the side surface 11a of the pillar 11. Accordingly, the silicon wafer 40 on which a plurality of fine structure portions 7 have been formed is obtained.

The same can be manufactured by using an SOI wafer. Further, a material of the pillar 11 is not limited to silicon, and a material of the sacrificial layer 13 is not limited to $SiO_2$. For the material of the pillar 11 and the material of the sacrificial layer 13, the sacrificial layer 13 is selectively etched with respect to the pillar 11. Further, it is unnecessary for the material of the substrate 4 to be the same as the material of the distal end portion of the pillar 11. For example, the substrate 4 may be a silicon wafer, the sacrificial layer may be $SiO_2$, and the distal end portion of the pillar 11 may be a resin. When the distal end portion of the pillar 11 is the resin, a nanoimprinting method may be used for formation.

This process is a first step of forming, on the surface 4a of the substrate 4, the fine structure portions 7 having the plurality of pillars 11 in which the plurality of grooves 12 are provided in the respective side surfaces 11a.

Subsequently, a metal such as Au or Ag is deposited on the silicon wafer 40 to form a conductor layer 6 using a vapor deposition method such as resistive heating evaporation or electron beam evaporation. In this case, a plurality of gaps G are formed in the conductor layer 6 constituting the optical functional portion 10. This step is a second step of forming the conductor layer 6 constituting the optical functional portion 10 that causes surface-enhanced Raman scattering, on the fine structure portion 7 using vapor phase growth. In the second step, the vapor phase growth is stopped in a state in which at least a portion of the inner surface 12a of each groove 12 is exposed, before the entire inner surface 12a of each groove 12 is covered with the conductor layer 6.

Subsequently, the silicon wafer 40 is cut for each fine structure portion 7 (in other words, for each optical functional portion 10) to obtain a plurality of SERS elements 3. In order to obtain the SERS unit 1, the SERS elements 3 manufactured as described above may be attached on the handling substrate 2.

As described above, in the method of manufacturing the SERS element 3 of the second embodiment, the vapor phase growth for forming the conductor layer 6 on the fine structure portion 7 is stopped in a state in which at least a portion of the inner surface 12a of each groove 12 is exposed before the conductor layer 6 covers the entire inner surface 12a of each groove 12. Accordingly, it is difficult for the opening of the groove 12 to be blocked by the conductor layer 6, and it is easy for the gap G preferably functioning as a nanogap to be formed in the portion corresponding to the groove 12 in the conductor layer 6, as illustrated in FIG. 12. In this case, since a thickness of the conductor layer 6 is small, it is easy for a desired gap G according to a shape of the groove 12 to be formed. Further, it is easy for the gap G preferably functioning as a nanogap to be formed in a portion corresponding to the base end portion 11b of the pillar 11 (a corner portion between the side surface 11a of the pillar 11 and the surface 4a of the substrate 4) in the conductor layer 6. That is, in the portion corresponding to the base end portion 11b of the pillar 11, the gap G which opens on the opposite side of the substrate 4 is formed to surround each pillar 11 when viewed from a direction in which the pillar 11 projects (that is, a thickness direction of the substrate 4) by the conductor layer 6 along the side surface 11a of the pillar 11 and the conductor layer 6 along the surface 4a of the substrate 4. In a deepest portion of the gap G the conductor layer 6 along the side surface 11a of the pillar 11 and the conductor layer 6 along the surface 4a of the substrate 4 may be connected or may be separated (the surface 4a of the substrate 4 may be exposed in the deepest portion of the gap G). For example, in the portion corresponding to the base end portion 11b of the pillar 11, the gap G is formed in a groove shape which extends annularly to surround each pillar 11 when viewed from a direction in which the pillar 11 projects. As described above, according to the method of manufacturing the SERS element 3 of the second embodiment, it is possible to obtain the SERS element 3 in which the intensity of surface-enhanced Raman scattering can be increased using the preferable nanogaps.

Figure 15:
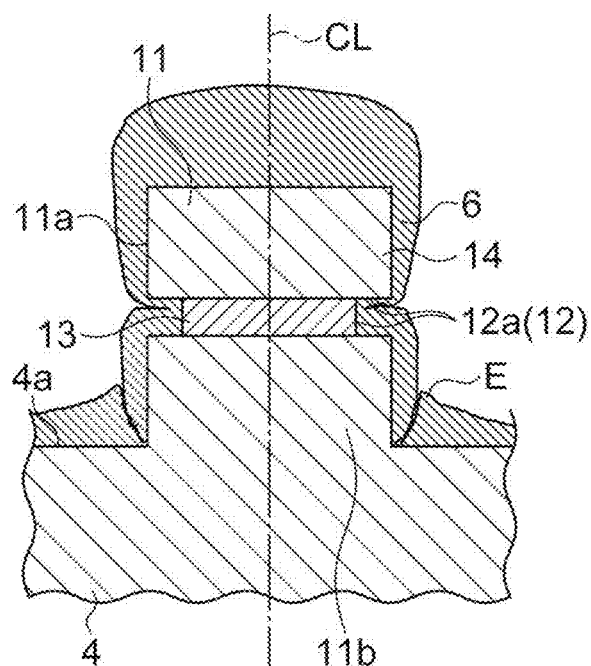
FIG. 15 is a cross-sectional view of a pillar and a conductor layer of a surface-enhanced Raman scattering element of a comparative example.

If vapor phase growth for forming the conductor layer 6 on the fine structure portion 7 is continued until the conductor layer 6 covers the entire inner surface 12a of each groove 12, a raised portion E (a portion raised by depositing a large amount of conductor in a portion in which the conductor layer 6 along the side surface 11a of the pillar 11 and the conductor layer 6 along the surface 4a of the substrate 4 meet) is formed in a portion corresponding to the base end portion 11b of the pillar 11 in the conductor layer 6 as illustrated in FIG. 15, and it is difficult for the gap G preferably functioning as the nanogap to be formed.

Further, since vapor deposition that is vapor phase growth with excellent anisotropy is performed as the vapor phase growth for forming the conductor layer 6 on the fine structure portion 7, it is possible to inhibit the conductor layer 6 from entering each groove 12 and form the gap G preferably functioning as a nanogap in the portion corresponding to the groove 12 in the conductor layer 6. Further, in a vapor deposition method that is a vapor phase growth method with excellent anisotropy, if conductor particles (conductive particles) are deposited from the direction in which the pillar 11 projects, it is easy for the conductive particles to be adhered on the surface 4a of the substrate 4 and in the vicinity of a distal end (near the top) of the pillar 11, whereas it is difficult for the conductive particles to reach a base of the pillar 11 (a portion corresponding to the base end portion 11b of the pillar 11) due to a shadowing effect by the conductive particles adhered in the vicinity of the distal end of the pillar 11. Therefore, it is possible to inhibit the raised portion E from being formed in the portion corresponding to the base end portion 11b of the pillar 11 and to form the gap G preferably functioning as a nanogap.

Since it is possible to easily change the width of the groove 12 only through adjustment of a thickness and a position of the sacrificial layer 13, and it is possible to easily change the depth of the groove 12 only through adjustment of etching conditions of a surface layer of the sacrificial layer 13, the SERS element 3 in which preferable nanogaps that can increase the intensity of surface-enhanced Raman scattering have been formed can be manufactured with good yield.

Figure 16:
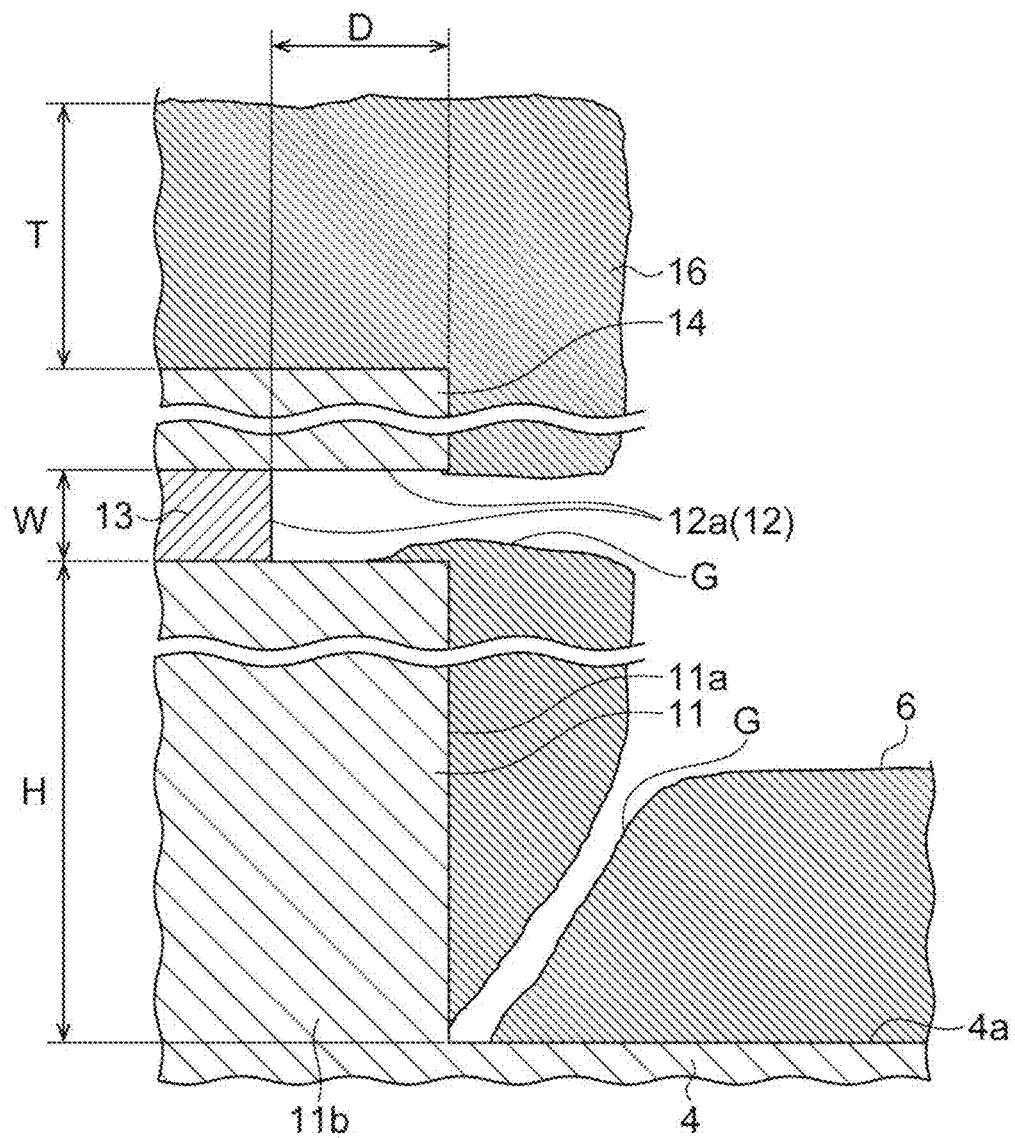
FIG. 16 is a cross-sectional view of a portion of the pillar and the conductor layer of FIG. 12.

Next, examples of dimensions will be described. As described above, when the plurality of pillars 11 having a columnar shape having a diameter and a height of several nm to hundreds of nm are periodically arranged at a pitch of tens of nm to hundreds of nm (preferably, 250 nm to 800 nm) along the surface 4a of the substrate 4 in the fine structure portion 7, the groove 12 has a width and depth of several nm to tens of nm, and the conductor layer 6 has a thickness of several nm to several μm. In this case, the gap G has an interval of about 0 to tens of nm. However, it is preferable that a width W of the groove 12 is set as a width corresponding to about 1/200 to 1 of the thickness of the conductor layer 6, and a depth D of the groove 12 is set as a "depth satisfying $D/W \geq 1$" as illustrated in FIG. 16, in consideration of the gap G preferably functioning as a nanogap being formed in the portion corresponding to each of the groove 12 and the base end portion 11b of the pillar 11 in the conductor layer 6 as illustrated in FIG. 12. It is preferable for the thickness T of the conductor layer 6 to be several nm to hundreds of nm. Accordingly, the gaps G having intervals of several Å to tens of nm are formed in the portion corresponding to each of the groove 12 and the base end portion 11b of the pillar 11 in the conductor layer 6. A height H of the groove 12 from the surface 4a of the substrate 4 is equal to or greater than a thickness T of the conductor layer 6 so that the grooves 12 is not buried in the conductor layer 6 formed on the surface 4a of the substrate 4.

Figure 17:
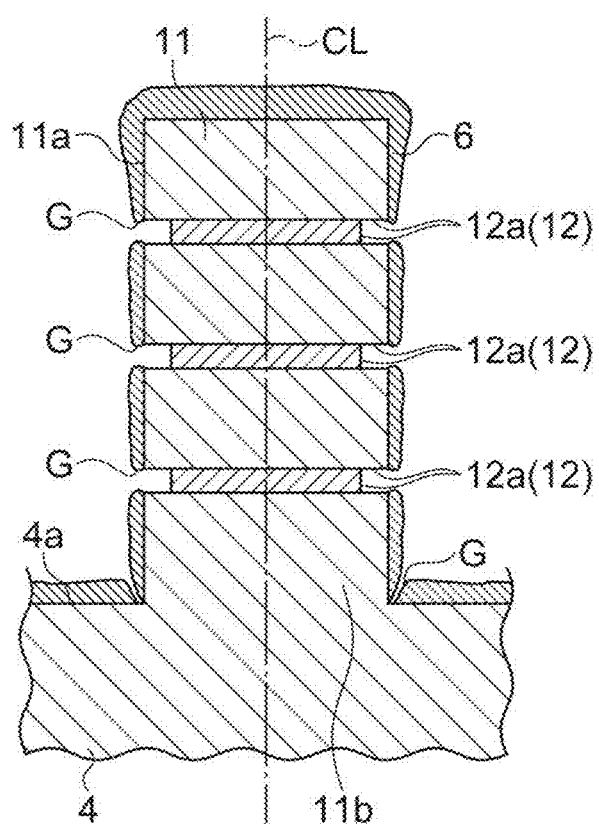
FIG. 17 is a cross-sectional view of a pillar and a conductor layer of a first modification example of the surface-enhanced Raman scattering element of the second embodiment of the present invention.

Next, a modification example of the SERS element 3 of the second embodiment will be described. As illustrated in FIG. 17, a plurality of grooves 12 may be provided for one pillar 11, for example, arranged side by side along the center line CL. According to this configuration, it is possible to increase the number of gaps G preferably functioning as nanogaps.

Figure 18:
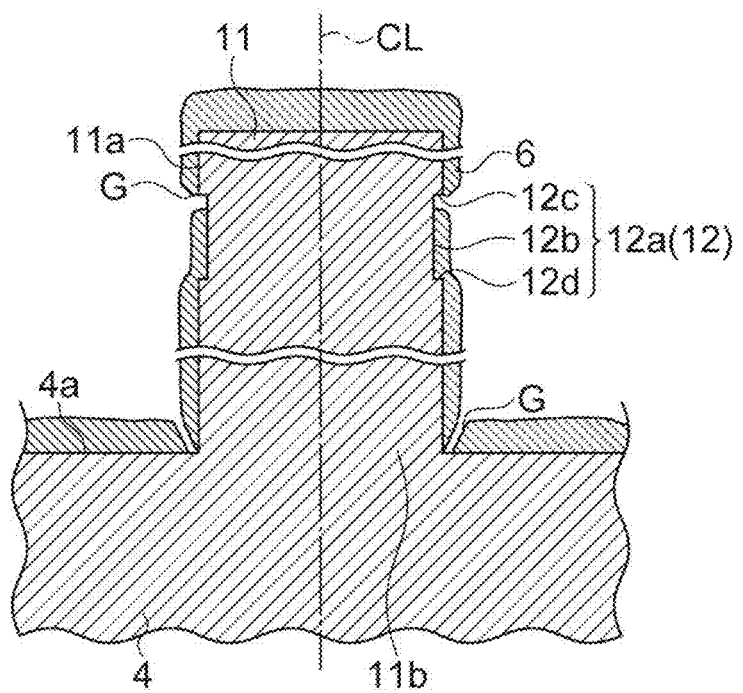
FIG. 18 is a cross-sectional view of a pillar and a conductor layer of a second modification example of the surface-enhanced Raman scattering element of the second embodiment of the present invention.

Further, as illustrated in FIG. 18, the groove 12 may be formed in the pillar 11 so that the depth of the groove 12 (a distance between the side surface 11a of the pillar 11 and the bottom surface 12b of the groove 12) is smaller than the width of the groove 12 (a distance between facing side surfaces 12c and 12d of the groove 12). That is, the groove 12 may be formed in the pillar 11 so that the depth D of the groove 12 and the width W of the groove 12 satisfy $D/W<1$. As examples of dimensions, it is preferable that the depth D of the groove 12 is set to several Å to hundreds of nm, and the width W of the groove 12 is set to tens of Å to several μm (more preferably, about 1 nm to 3 μm). However, the width W of the groove 12 needs to be greater than the thickness of the conductor layer 6. Accordingly, the gaps G having intervals of several Å to tens of nm are formed in the portion corresponding to each of the groove 12 and the base end portion 11b of the pillar 11 in the conductor layer 6.

The groove 12 is formed in the pillar 11 so that the depth of the groove 12 is smaller than the width of the groove 12, making it possible to decrease the diameter of the pillar 11, and a distance (pitch) between adjacent pillars 11 and, as a result, improving a degree of freedom in dimensioning. In the portion corresponding to the groove 12 in the conductor layer 6, a region of the bottom surface 12b of the groove 12 on the distal end side of the pillar 11, and the side surface 12c of the groove 12 on the distal end side of the pillar 11 are exposed, and the gap G is formed in this portion.

Figure 19:
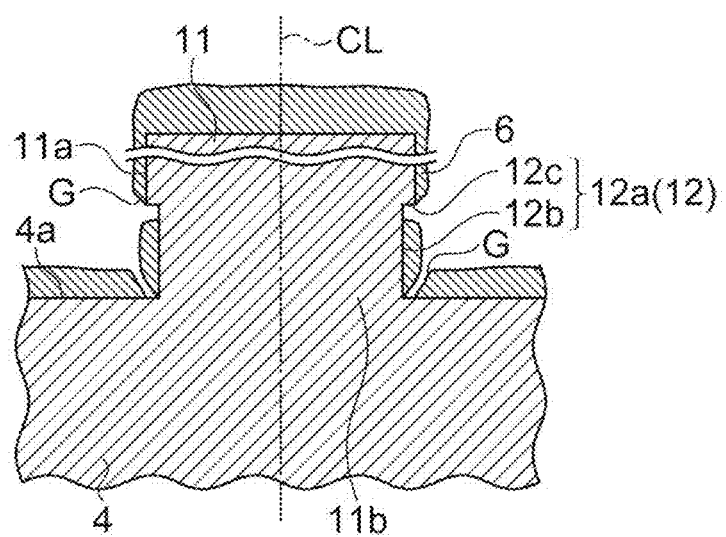
FIG. 19 is a cross-sectional view of a pillar and a conductor layer of a third modification example of the surface-enhanced Raman scattering element of the second embodiment of the present invention.

Further, as illustrated in FIG. 19, the groove 12 may be formed in the base end portion 11b of the pillar 11. The groove 12 may be formed in the base end portion 11b of the pillar 11 so that the thickness of the conductor layer 6 is smaller than the width of the groove 12 (a distance between the side surface 12c of the groove 12 and the surface 4a of the substrate that face each other). In this case, it is easy for the gap G to be formed in a portion corresponding to both sides in a width direction of the groove 12 in the conductor layer 6. That is, it is possible to increase the number of gaps G formed in one groove 12. Further, when the conductor layer 6 is formed using vapor deposition, it is possible to increase an effect of the conductor layer 6 adhered to the side surface 11a of the pillar 11 on the upper side from the groove 12 being an umbrella (shadowing effect). Accordingly, it is easy for the gap G to be formed in a portion corresponding to the base end portion 11b of the pillar 11 in the conductor layer 6.

Further, the distance between the gaps G formed in the portions corresponding to both sides in the width direction of the groove 12 in the conductor layer 6 can be easily controlled by adjusting the width of the groove 12. As a result, the gap G can be efficiently and effectively arranged in the conductor layer 6 according to a positional distribution of measurement molecules adsorbed on the conductor layer 6 formed on the pillar 11. For example, if the distance between the gaps G formed in the portions corresponding to both sides in the width direction of the groove 12 in the conductor layer 6 is increased by increasing the width of the groove 12, the gap G on the distal end side of the pillar 11 is formed on the relatively upper side of the pillar 11. Accordingly, a large number of molecules easily adsorbed on the upper side of the pillar 11 are attached in the vicinity of the gap G on the distal end side of the pillar 11, making it possible to effectively increase surface-enhanced Raman scattering light. On the other hand, if the distance between the gaps G formed in the portions corresponding to both sides in the width direction of the groove 12 in the conductor layer 6 is decreased by decreasing the width of the groove 12, the gap G on the distal end side of the pillar 11 is formed on the relatively lower side of the pillar 11. Accordingly, molecules easily adsorbed on the lower side of the pillar 11 are attached in the vicinity of the gap G on the distal end side of the pillar 11 and the gap G on the base end side of the pillar 11, making it possible to effectively increase surface-enhanced Raman scattering light. For example, when the SERS element 3 is reversed, immersed in the solution sample, and then dried so that measurement molecules are adsorbed, the measurement molecules are expected to be arranged on the upper side of the pillar 11 if there is less solution sample. Accordingly, the width of the grooves 12 increases. On the other hand, when a small amount of solution sample is dropped onto the SERS element 3, the measurement molecules are expected to be arranged on the lower side of the pillar 11. Accordingly, the width of the groove 12 decreases.

Third Embodiment

Figure 20:
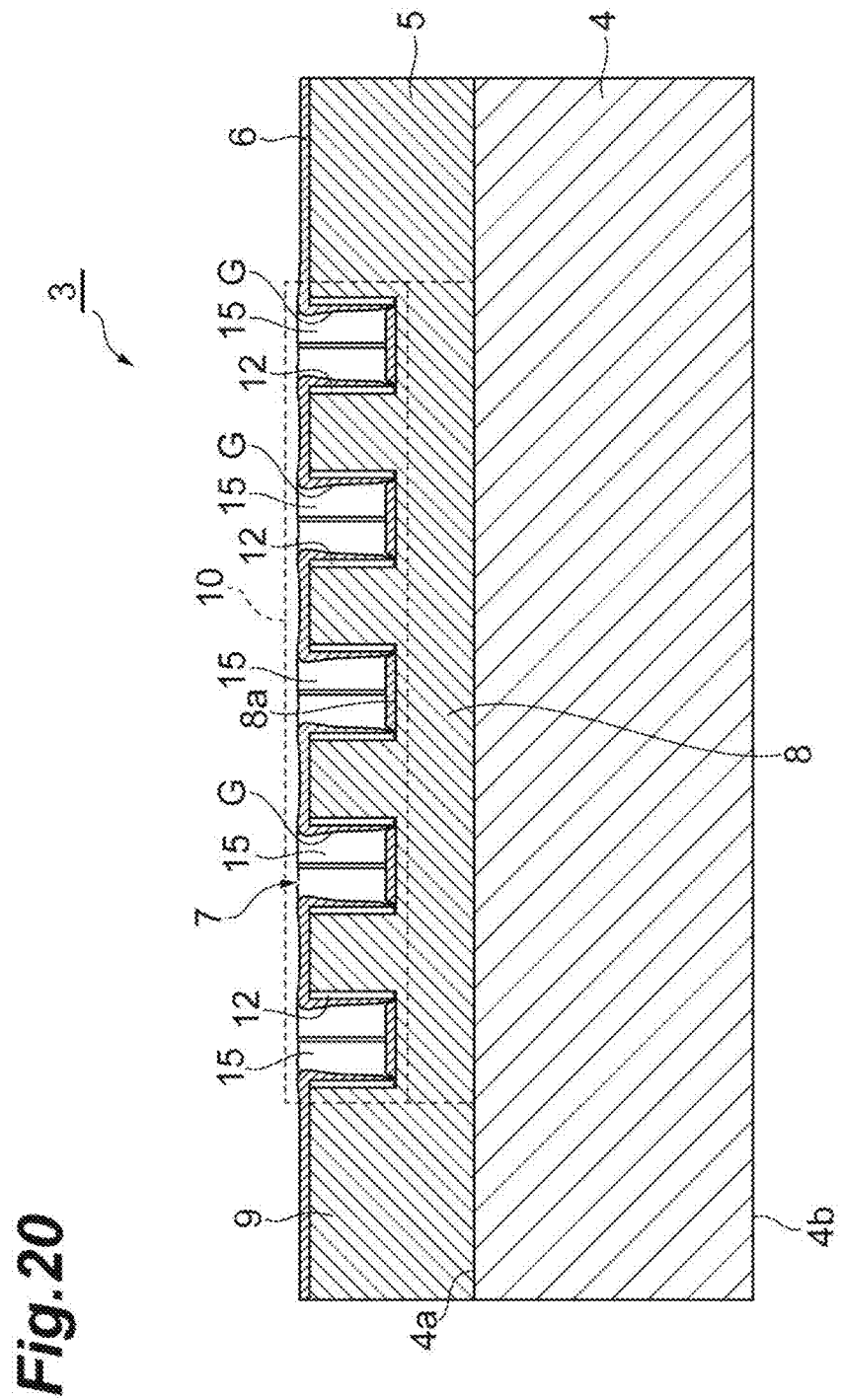
FIG. 20 is a cross-sectional view of a surface-enhanced Raman scattering element according to a third embodiment of the present invention.

As illustrated in FIG. 20, an SERS element 3 of a third embodiment is mainly different from the SERS element 3 of the first embodiment described above in that a hole (a depression) 15 is formed in a molded layer 5 in place of the pillar 11. In the SERS element 3 of the third embodiment, a plurality of holes 15 with a columnar shape having a diameter and a depth of several nm to hundreds of nm are periodically arranged at a pitch of tens of nm to hundreds of nm (preferably, 250 nm to 800 nm) along the surface 4a of the substrate 4 in a fine structure portion 7.

The conductor layer 6 is formed from the fine structure portion 7 to the frame portion 9. In the fine structure portion 7, the conductor layer 6 reaches the surface 8a of the support portion 8 (that is, the bottom surface of each hole 15) exposed on the opposite side of the substrate 4. In the SERS element 3, the conductor layer 6 formed on the fine structure portion 7 and the surface 8a of the support portion 8 constitutes the optical functional portion 10 that causes surface-enhanced Raman scattering.

Figure 21:
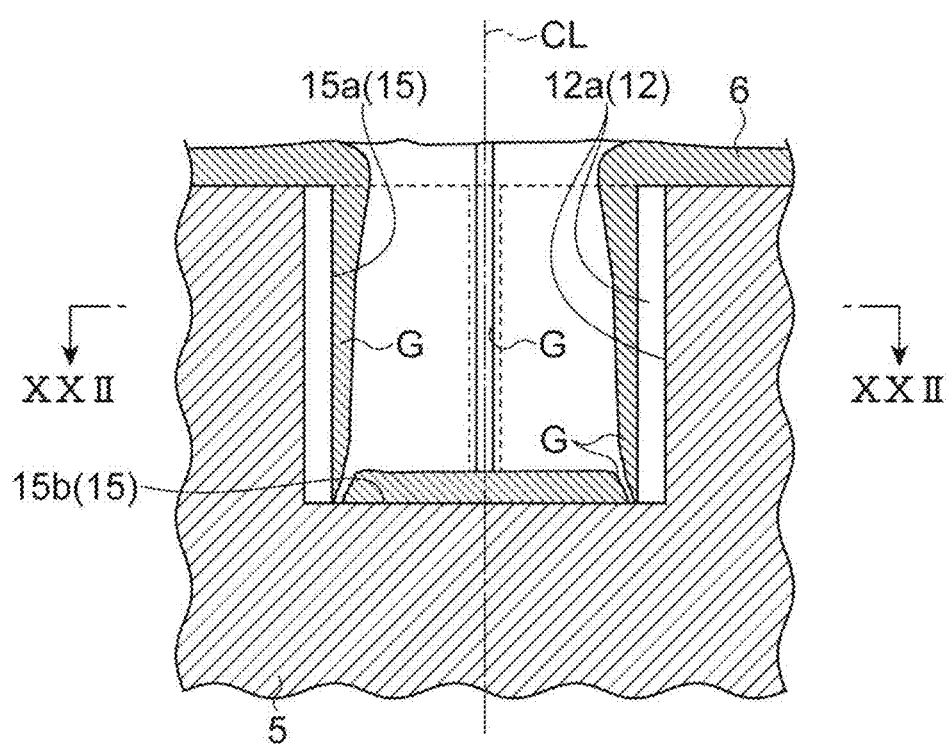
FIG. 21 is a cross-sectional view of a hole and a conductor layer of FIG. 20.
Figure 22:
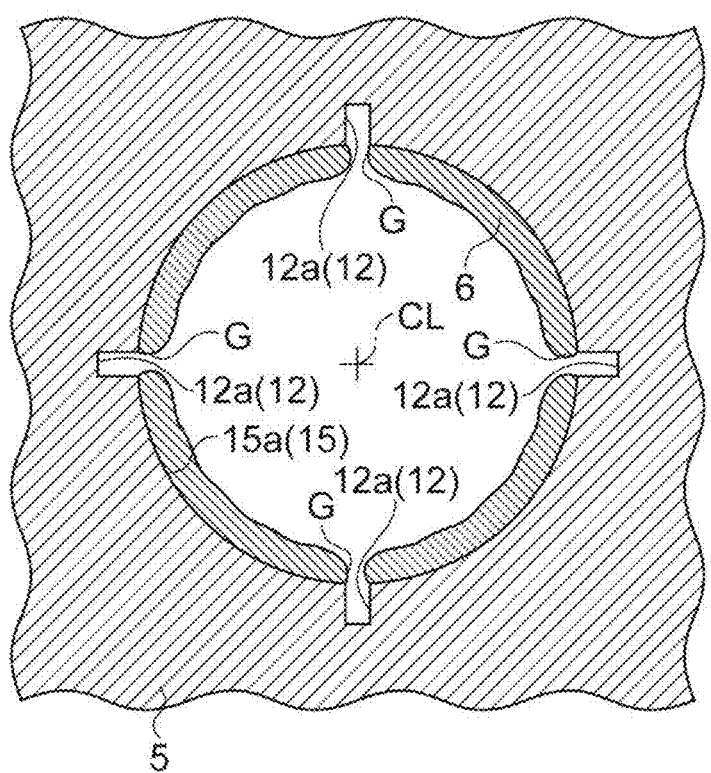
FIG. 22 is a cross-sectional view of the hole and the conductor layer taken along line XXII-XXII in FIG. 21.

As illustrated in FIGS. 21 and 22, a rectangular sectional groove 12 is provided on the side surface (inner surface) 15a of each hole 15. The groove 12 extends along the center line CL of the hole 15, and a plurality of grooves (in the SERS element 3 of the third embodiment, one groove every 90° with respect to the center line CL for a total of four) are provided for one hole 15. The conductor layer 6 is formed on the side surface 15a and a bottom surface (inner surface) 15b of each hole 15. The conductor layer 6 does not cover an entire inner surface 12a of the groove 12 and does not completely cover an opening of the groove 12. That is, at least a portion of the inner surface 12a of the groove 12 is exposed to the outside of the groove 12. In the conductor layer 6, the conductor layer 6 is formed on the side surface 15a of each hole 15 in a state in which at least a portion of the inner surface 12a of each groove 12 is exposed and, accordingly, a plurality of gaps G are formed. That is, in the conductor layer 6 constituting the optical functional portion 10, the conductor layer 6 along the side surface 15a of the hole 15 is separated by the groove 12, and the gap G is formed along each groove 12. The center line CL of the hole 15 is a line passing through a centroid with respect to each cross-sectional shape of the hole 15 perpendicular to the center line CL.

As described above, in the SERS element 3 of the third embodiment, the conductor layer 6 is formed on the side surface 15a of each hole 15 in a state in which at least a portion of the inner surface 12a of each groove 12 is exposed, and accordingly, the plurality of gaps G are formed in the conductor layer 6 constituting the optical functional portion 10. The gap G formed in the conductor layer 6 preferably functions as a nanogap. Therefore, according to the surface-enhanced Raman scattering element 3 of the third embodiment, it is possible to increase the intensity of the surface-enhanced Raman scattering using the preferable nanogaps.

Further, since the plurality of holes 15 are periodically arranged along the surface 4a of the substrate 4, it is possible to stably increase the intensity of the surface-enhanced Raman scattering.

Further, since a plurality of grooves 12 are provided for one hole 15, it is possible to increase the number of gaps G preferably functioning as nanogaps.

Next, a method of manufacturing the SERS element 3 of the third embodiment will be described. First, a step of obtaining the silicon wafer 40 in which a plurality of fine structure portions 7 are formed, that is, the first step of forming, on the surface 4a of the substrate 4, the fine structure portions 7 having the plurality of holes 15 in which the plurality of grooves 12 are provided in the respective side surfaces 15a is performed by forming the fine structure portion 7 on the molded layer 5 using a nanoimprinting method, similar to the method of manufacturing the SERS element 3 of the first embodiment described above. The fine structure portion 7 may be formed on the substrate 4 by etching using a mask having a pattern having a two-dimensional shape (a mask obtained by inverting a mask portion and an opening portion of the mask of the first embodiment described above).

Subsequently, a metal such as Au or Ag is deposited on the molded layer 5 to form a conductor layer 6 using a vapor deposition method such as resistive heating evaporation or electron beam evaporation. In this case, a plurality of gaps G are formed in the conductor layer 6 constituting the optical functional portion 10. This step is a second step of forming the conductor layer 6 constituting the optical functional portion 10 that causes surface-enhanced Raman scattering, on the fine structure portion 7 using vapor phase growth. In the second step, the vapor phase growth is stopped in a state in which at least a portion of the inner surface 12a of each groove 12 is exposed, before the entire inner surface 12a of each groove 12 is covered with the conductor layer 6.

Subsequently, the silicon wafer 40 is cut for each fine structure portion 7 (in other words, for each optical functional portion 10) to obtain a plurality of SERS elements 3. In order to obtain the SERS unit 1, the SERS elements 3 manufactured as described above may be attached on the handling substrate 2.

As described above, in the method of manufacturing the SERS element 3 of the third embodiment, the vapor phase growth for forming the conductor layer 6 on the fine structure portion 7 is stopped in a state in which at least a portion of the inner surface 12a of each groove 12 is exposed before the conductor layer 6 covers the entire inner surface 12a of each groove 12. Accordingly, it is difficult for the opening of the groove 12 to be blocked by the conductor layer 6, and it is easy for the gap G preferably functioning as a nanogap to be formed in the portion corresponding to the groove 12 in the conductor layer 6, as illustrated in FIG. 21. In this case, since a thickness of the conductor layer 6 is small, it is easy for a desired gap G according to a shape of the groove 12 to be formed. Further, it is easy for the gap G preferably functioning as a nanogap to be formed in a portion corresponding to the bottom portion of the hole 15 (a corner portion between the side surface 15a of the hole 15 and the bottom surface 15b of the hole 15) in the conductor layer 6. That is, in the portion corresponding to the bottom portion of the hole 15, the gap G which opens on the opposite side of the substrate 4 is formed to surround each center line CL when viewed from a direction in which the center line CL of the hole 15 extends (that is, a thickness direction of the substrate 4) by the conductor layer 6 along the side surface 15a of the hole 15 and the conductor layer 6 along the bottom surface 15b of the hole 15. In a deepest portion of the gap G, the conductor layer 6 along the side surface 15a of the hole 15 and the conductor layer 6 along the bottom surface 15b of the hole 15 may be connected or may be separated (the bottom surface 15b of the hole 15 may be exposed in the deepest portion of the gap G). For example, in the portion corresponding to the bottom portion of the hole 15, the gap G is formed in a groove shape which extends annularly to surround each center line CL when viewed from a direction in which the center line CL of the hole 15 extends. As described above, according to the method of manufacturing the SERS element 3 of the third embodiment, it is possible to obtain the SERS element 3 in which the intensity of surface-enhanced Raman scattering can be increased using the preferable nanogaps.

Figure 23:
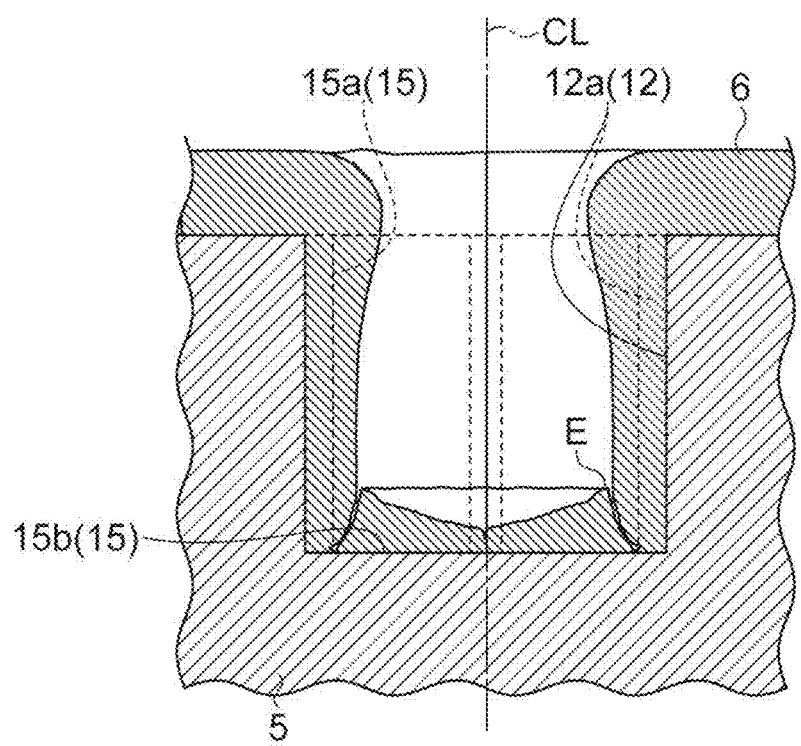
FIG. 23 is a cross-sectional view of a hole and a conductor layer of a surface-enhanced Raman scattering element of a comparative example.

If vapor phase growth for forming the conductor layer 6 on the fine structure portion 7 is continued until the conductor layer 6 covers the entire inner surface 12a of each groove 12, a raised portion E (a portion raised by depositing a large amount of conductor in a portion in which the conductor layer 6 along the side surface 15a of the hole 15 and the conductor layer 6 along the bottom surface 15b of the hole 15 meet) is formed in a portion corresponding to the bottom portion of the hole 15 in the conductor layer 6 as illustrated in FIG. 23, and it is difficult for the gap G preferably functioning as the nanogap to be formed.

Further, since vapor deposition that is vapor phase growth with excellent anisotropy is performed as the vapor phase growth for forming the conductor layer 6 on the fine structure portion 7, it is possible to inhibit the conductor layer 6 from entering each groove 12 and form the gap G preferably functioning as a nanogap in the portion corresponding to the groove 12 in the conductor layer 6. Further, in a vapor deposition method that is a vapor phase growth method with excellent anisotropy, if conductor particles (conductive particles) are deposited from an opening side of the hole 15, it is easy for the conductive particles to be adhered on the bottom surface 15b of the hole 15 and in the vicinity of the opening of the hole 15, whereas it is difficult for the conductive particles to reach the portion corresponding to the bottom portion of the hole 15 (a corner portion between the side surface 15a of the hole 15 and the bottom surface 15b of the hole 15) due to a shadowing effect by the conductive particles adhered in the vicinity of the opening of the hole 15. Therefore, it is possible to inhibit the raised portion E from being formed in the portion corresponding to the bottom portion of the hole 15 and to form the gap G preferably functioning as a nanogap.

In examples of dimensions, it is preferable that a width W of the groove 12 is set as a width corresponding to about 1/200 to about 1 of the thickness of the conductor layer 6, and a depth D of the groove 12 is set to 1 nm to hundreds of nm {a depth corresponding to less than 1/2 of a distance (pitch) between the adjacent holes 15}, similar to the SERS element 3 of the first embodiment (see FIG. 10), in consideration of the gap G preferably functioning as a nanogap being formed in the portion corresponding to each of the groove 12 and the bottom portion of the hole 15 in the conductor layer 6 as illustrated in FIG. 21. It is preferable for the thickness T of the conductor layer 6 to be several nm to hundreds of nm. Accordingly, the gaps G having intervals of several Å to tens of nm are formed in the portion corresponding to each of the groove 12 and the bottom portion of the hole 15 in the conductor layer 6.

Fourth Embodiment

Figure 24:
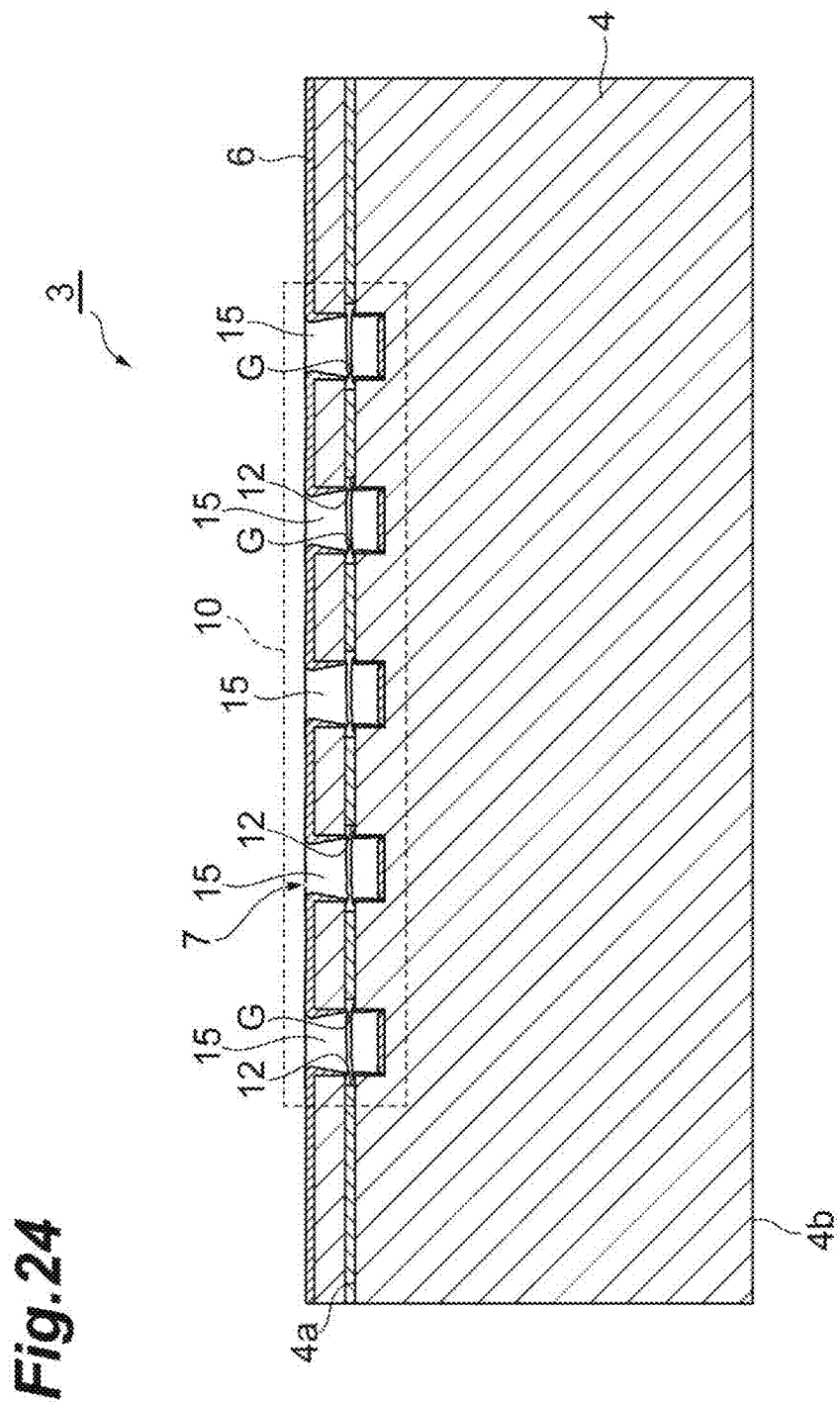
FIG. 24 is a cross-sectional view of a surface-enhanced Raman scattering element according to a fourth embodiment of the present invention.
Figure 25:
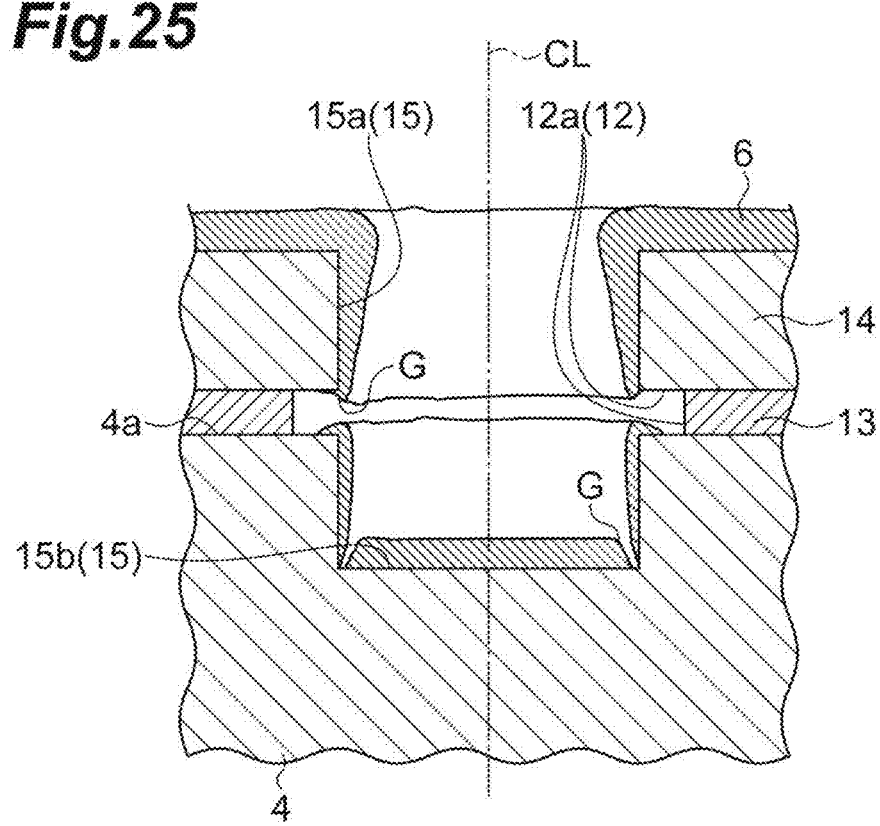
FIG. 25 is a cross-sectional view of the hole and the conductor layer of FIG. 24.

As illustrated in FIG. 24, an SERS element 3 of a fourth embodiment primarily differs from the SERS element 3 of the third embodiment described above in that a fine structure portion 7 is formed in a surface 4a of a substrate 4, and a groove 12 extends to surround a center line CL of a hole 15 (see FIG. 25). In the SERS element 3 of the fourth embodiment, the fine structure portion 7 is formed in a central portion of the surface 4a of the substrate 4, and has an appearance having a rectangular shape of hundreds of μm×hundreds of μm to tens of mm×tens of mm when viewed from a thickness direction of the substrate 4. Holes 15 of the fine structure portion 7 are periodically arranged at a pitch of tens of nm to hundreds of nm (preferably, 250 nm to 800 nm) along the surface 4a of the substrate 4.

The conductor layer 6 is formed from the fine structure portion 7 to the surface 14a of the surface layer 14. The conductor layer 6 reaches the surface of the substrate 4 (that is, the bottom surface of each hole 15) exposed at the fine structure portion 7. In the SERS element 3, the conductor layer 6 formed on the fine structure portion 7 and the surface of the substrate 4 exposed in the fine structure portion 7 constitutes the optical functional portion 10 causing surface-enhanced Raman scattering.

As illustrated in FIG. 25, the groove 12 extends annularly to surround the center line CL of the hole 15 and one groove 12 is provided for one hole 15. The conductor layer 6 is formed on the side surface 15a and a bottom surface (inner surface) 15b of each hole 15. The conductor layer 6 does not cover an entire inner surface 12a of the groove 12 and does not completely cover an opening of the groove 12. That is, at least a portion of the inner surface 12a of the groove 12 is exposed to the outside of the groove 12. In the conductor layer 6, the conductor layer 6 is formed on the side surface 15a of each hole 15 in a state in which at least a portion of the inner surface 12a of each groove 12 is exposed and, accordingly, a plurality of gaps G are formed. That is, in the conductor layer 6 constituting the optical functional portion 10, the conductor layer 6 along the side surface 15a of the hole 15 is separated by the groove 12, and the gap G is formed along each groove 12.

As described above, in the SERS element 3 of the fourth embodiment, the conductor layer 6 is formed on the side surface 15a of each hole 15 in a state in which at least a portion of the inner surface 12a of each groove 12 is exposed, and accordingly, the plurality of gaps G are formed in the conductor layer 6 constituting the optical functional portion 10. The gap G formed in the conductor layer 6 preferably functions as a nanogap. Therefore, according to the surface-enhanced Raman scattering element 3 of the fourth embodiment, it is possible to increase the intensity of the surface-enhanced Raman scattering using the preferable nanogaps.

Further, since the plurality of holes 15 are periodically arranged along the surface 4a of the substrate 4, it is possible to stably increase the intensity of the surface-enhanced Raman scattering.

A plurality of grooves 12 may be provided for one hole 15, for example, arranged side by side along the center line CL. According to this configuration, it is possible to increase the number of gaps G preferably functioning as nanogaps.

Further, the groove 12 may be formed in the hole 15 so that the depth of the groove 12 (a distance between the side surface 15a of the hole 15 and the bottom surface of the groove 12) is smaller than the width of the groove 12 (a distance between facing side surfaces of the groove 12). That is, the groove 12 may be formed in the hole 15 so that the depth D of the groove 12 and the width W of the groove 12 satisfy D/W<1. As examples of dimensions, it is preferable that the depth D of the groove 12 is set to several Å to hundreds of nm, and the width W of the groove 12 is set to tens of Å to several μm (more preferably, about 1 nm to 3 μm). However, the width W of the groove 12 needs to be greater than the thickness of the conductor layer 6. Accordingly, the gaps G having intervals of several Å to tens of nm are formed in the portion corresponding to each of the groove 12 and the bottom portion of the hole 15 in the conductor layer 6.

The groove 12 is formed in the hole 15 so that the depth of the groove 12 is smaller than the width of the groove 12, making it possible to decrease the diameter of the hole 15, and a distance (pitch) between adjacent holes 15 and, as a result, improving a degree of freedom in dimensioning. In the portion corresponding to the groove 12 in the conductor layer 6, a region of the bottom surface of the groove 12 on the opening side of the hole 15, and the side surface of the groove 12 on the opening side of the hole 15 are exposed, and the gap G is formed in this portion.

Further, the grooves 12 may be formed in the bottom portion of the hole 15. The grooves 12 may be formed in the bottom portion of the hole 15 so that the thickness of the conductor layer 6 is smaller than the width of the groove 12 (the distance between the side surface of the groove 12 and the bottom surface 15b of the hole 15 that face each other). In this case, it is easy for the gap G to be formed in a portion corresponding to both sides in a width direction of the groove 12 in the conductor layer 6. That is, it is possible to increase the number of gaps G formed in one groove 12. Further, when the conductor layer 6 is formed using vapor deposition, it is possible to increase an effect of the conductor layer 6 adhered to the side surface 15a of the hole 15 on the upper side from the groove 12 being an umbrella. Accordingly, it is easy for the gap G to be formed in a portion corresponding to the bottom portion of the hole 15 in the conductor layer 6.

Further, the distance between the gaps G formed in the portions corresponding to both sides in the width direction of the groove 12 in the conductor layer 6 can be easily controlled by adjusting the width of the groove 12. As a result, the gap G can be efficiently and effectively arranged in the conductor layer 6 according to a positional distribution of measurement molecules adsorbed on the conductor layer 6 formed on the hole 15. For example, if the distance between the gaps G formed in the portions corresponding to both sides in the width direction of the groove 12 in the conductor layer 6 is increased by increasing the width of the groove 12, the gap G on the distal end side of the hole 15 is formed on the relatively upper side of the hole 15. Accordingly, a large number of molecules easily adsorbed on the upper side of the hole 15 are attached in the vicinity of the gap G on the distal end side of the hole 15, making it possible to effectively increase surface-enhanced Raman scattering light. On the other hand, if the distance between the gaps G formed in the portions corresponding to both sides in the width direction of the groove 12 in the conductor layer 6 is decreased by decreasing the width of the groove 12, the gap G on the distal end side of the hole 15 is formed on the relatively lower side of the hole 15. Accordingly, molecules easily adsorbed on the lower side of the hole 15 are attached in the vicinity of the gap G on the distal end side of the hole 15 and the gap G on the base end side of the hole 15, making it possible to effectively increase surface-enhanced Raman scattering light. For example, when the SERS element 3 is reversed, immersed in the solution sample, and then dried so that measurement molecules are adsorbed, the measurement molecules are expected to be arranged on the upper side of the hole 15 if there is less solution sample. Accordingly, the width of the grooves 12 increases. On the other hand, when a small amount of solution sample is dropped onto the SERS element 3, the measurement molecules are expected to be arranged on the lower side of the hole 15. Accordingly, the width of the groove 12 decreases.

Next, a method of manufacturing the SERS element 3 of the fourth embodiment will be described. First, a step of obtaining the silicon wafer 40 in which a plurality of fine structure portions 7 are formed, that is, the first step of forming, in the surface 4a of the substrate 4, the fine structure portions 7 having the plurality of holes 15 in which the plurality of grooves 12 are provided in the respective side surfaces 15a is performed by performing etching using a mask having a pattern having a two-dimensional shape, similar to the method of manufacturing the SERS element 3 of the second embodiment (a mask obtained by inverting a mask portion and an opening portion of the mask of the second embodiment described above).

Subsequently, a metal such as Au or Ag is deposited on the molded layer 5 to form a conductor layer 6 using a vapor deposition method such as resistive heating evaporation or electron beam evaporation. In this case, a plurality of gaps G are formed in the conductor layer 6 constituting the optical functional portion 10. This step is a second step of forming the conductor layer 6 constituting the optical functional portion 10 that causes surface-enhanced Raman scattering, on the fine structure portion 7 using vapor phase growth. In the second step, the vapor phase growth is stopped in a state in which at least a portion of the inner surface 12a of each groove 12 is exposed, before the entire inner surface 12a of each groove 12 is covered with the conductor layer 6.

Subsequently, the silicon wafer 40 is cut for each fine structure portion 7 (in other words, for each optical functional portion 10) to obtain a plurality of SERS elements 3. In order to obtain the SERS unit 1, the SERS elements 3 manufactured as described above may be attached on the handling substrate 2.

As described above, in the method of manufacturing the SERS element 3 of the fourth embodiment, the vapor phase growth for forming the conductor layer 6 on the fine structure portion 7 is stopped in a state in which at least a portion of the inner surface 12a of each groove 12 is exposed before the conductor layer 6 covers the entire inner surface 12a of each groove 12. Accordingly, it is difficult for the opening of the groove 12 to be blocked by the conductor layer 6, and it is easy for the gap G preferably functioning as a nanogap to be formed in the portion corresponding to the groove 12 in the conductor layer 6, as illustrated in FIG. 25. In this case, since a thickness of the conductor layer 6 is small, it is easy for a desired gap G according to a shape of the groove 12 to be formed. Further, it is easy for the gap G preferably functioning as a nanogap to be formed in a portion corresponding to the bottom portion of the hole 15 (a corner portion between the side surface 15a of the hole 15 and the bottom surface 15b of the hole 15) in the conductor layer 6. That is, in the portion corresponding to the bottom portion of the hole 15, the gap G which opens on the opposite side of the substrate 4 is formed to surround each center line CL when viewed from a direction in which the center line CL of the hole 15 extends (that is, a thickness direction of the substrate 4) by the conductor layer 6 along the side surface 15a of the hole and the conductor layer 6 along the bottom surface 15b of the hole 15. In a deepest portion of the gap CG the conductor layer 6 along the side surface 15a of the hole 15 and the conductor layer 6 along the bottom surface 15b of the hole 15 may be connected or may be separated (the bottom surface 15b of the hole 15 may be exposed in the deepest portion of the gap G). For example, in the portion corresponding to the bottom portion of the hole 15, the gap G is formed in a groove shape which extends annularly to surround each center line CL when viewed from a direction in which the center line CL of the hole 15 extends. As described above, according to the method of manufacturing the SERS element 3 of the fourth embodiment, it is possible to obtain the SERS element 3 in which the intensity of surface-enhanced Raman scattering can be increased using the preferable nanogaps.

Figure 26:
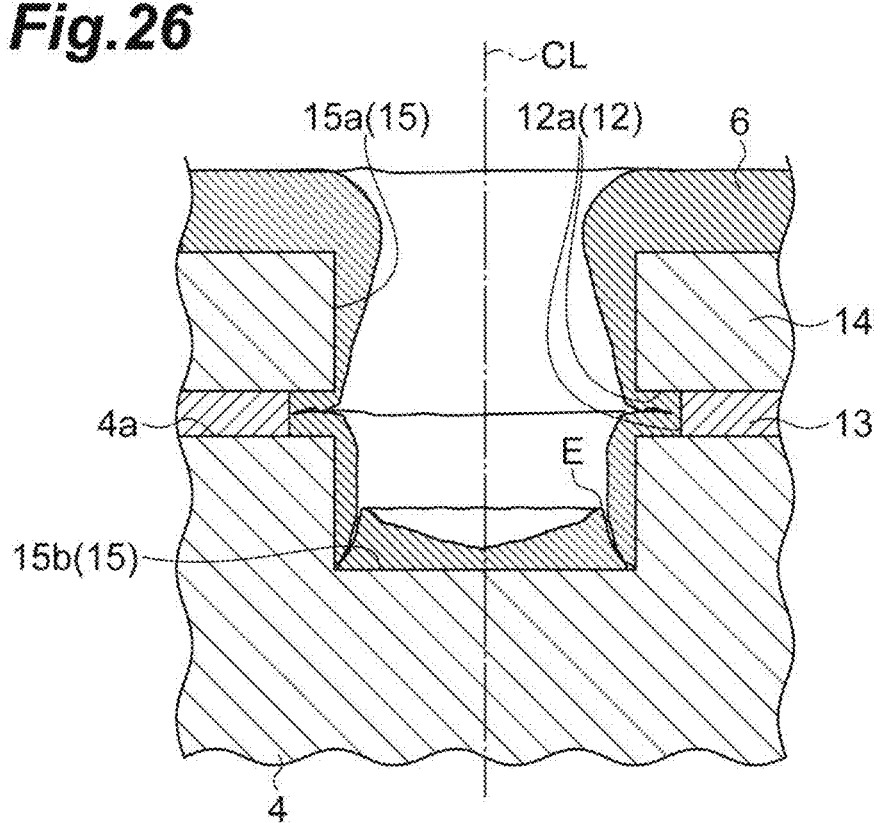
FIG. 26 is a cross-sectional view of a hole and a conductor layer of a surface-enhanced Raman scattering element of a comparative example.

If vapor phase growth for forming the conductor layer 6 on the fine structure portion 7 is continued until the conductor layer 6 covers the entire inner surface 12a of each groove 12, a raised portion E (a portion raised by depositing a large amount of conductor in a portion in which the conductor layer 6 along the side surface 15a of the hole 15 and the conductor layer 6 along the bottom surface 15b of the hole 15 meet) is formed in a portion corresponding to the bottom portion of the hole 15 in the conductor layer 6 as illustrated in FIG. 26, and it is difficult for the gap G preferably functioning as the nanogap to be formed.

Further, since vapor deposition that is vapor phase growth with excellent anisotropy is performed as the vapor phase growth for forming the conductor layer 6 on the fine structure portion 7, it is possible to inhibit the conductor layer 6 from entering each groove 12 and form the gap G preferably functioning as a nanogap in the portion corresponding to the groove 12 in the conductor layer 6. Further, in a vapor deposition method that is a vapor phase growth method with excellent anisotropy, if conductor particles (conductive particles) are deposited from the opening side of the hole 11, it is easy for the conductive particles to be adhered on the bottom surface 15b of the hole 15 and in the vicinity of the opening of the hole 15, whereas it is difficult for the conductive particles to reach the portion corresponding to the bottom portion of the hole 15 (a corner portion between the side surface 15a of the hole 15 and the bottom surface 15b of the hole 15) due to a shadowing effect by the conductive particles adhered in the vicinity of the opening of the hole 15. Therefore, it is possible to inhibit the raised portion E from being formed in the portion corresponding to the bottom portion of the hole 15 and to form the gap G preferably functioning as a nanogap.

In examples of dimensions, it is preferable that a width W of the groove 12 is set as a width corresponding to about ½₀₀ to about 1 of the thickness of the conductor layer 6, and a depth D of the groove 12 is set as a "depth satisfying D/W≥1", similar to the SERS element 3 of the second embodiment (see FIG. 16), in consideration of the gap G preferably functioning as a nanogap being formed in the portion corresponding to each of the groove 12 and the bottom portion of the hole 15 in the conductor layer 6 as illustrated in FIG. 25. It is preferable for the thickness T of the conductor layer 6 to be several nm to hundreds of nm. Accordingly, the gaps G having intervals of several Å to tens of nm are formed in the portion corresponding to each of the groove 12 and the bottom portion of the hole 15 in the conductor layer 6. A height H of the groove 12 from the bottom surface 15b of the hole 15 is equal to or greater than a thickness T of the conductor layer 6 so that the grooves 12 is not buried in the conductor layer 6 formed on the bottom surface 15b of the hole 15.

The first to fourth embodiments of the present invention have been described above, but the present invention is not limited to each of the above embodiments. For example, an arrangement structure of the pillars 11 and holes 15 is not limited to the two-dimensional arrangement, and may be a one-dimensional arrangement, and the arrangement structure is not limited to a square lattice arrangement and may be a triangular lattice arrangement. The cross-sectional shape of the pillar 11 and the hole 15 is not limited to a circle, and may be an ellipse or a polygon (a triangle, a rectangle, or the like). Thus, the material and shape of each configuration of the SERS element 3 and the SERS unit 1 are not limited to the above-described materials and shapes, and various materials and shapes can be applied.

Further, the fine structure portion 7 may be indirectly formed on the surface 4a of the substrate 4, for example, through the support portion 8, as in the first embodiment and the third embodiment, and may be directly formed on the surface 4a of the substrate 4 in the second embodiment and the fourth embodiment. Further, the conductor layer 6 is not limited to the conductor layer directly formed on the fine structure portion 7, and may be a conductor layer indirectly formed on the fine structure portion 7 through any layer such as a buffer metal (Ti, Cr, or the like) layer for improving the adhesion of a metal to the fine structure portion 7.

Figure 27:
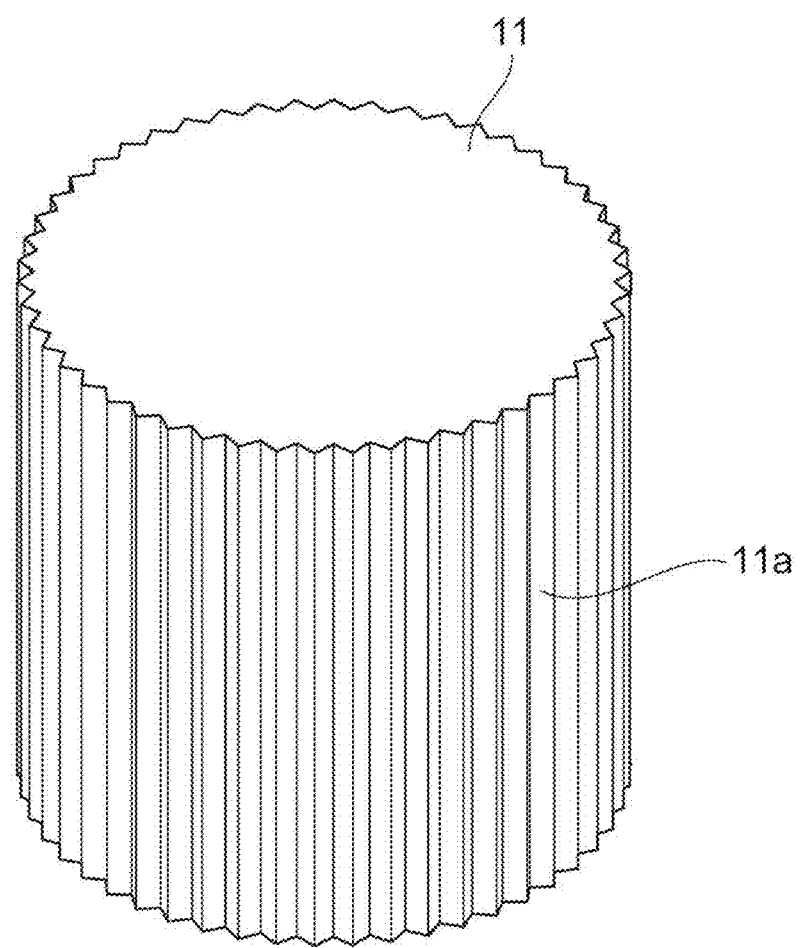
FIG. 27 is a cross-sectional view of a pillar of a first modification example of the surface-enhanced Raman scattering element of one embodiment of the present invention.
Figure 28:
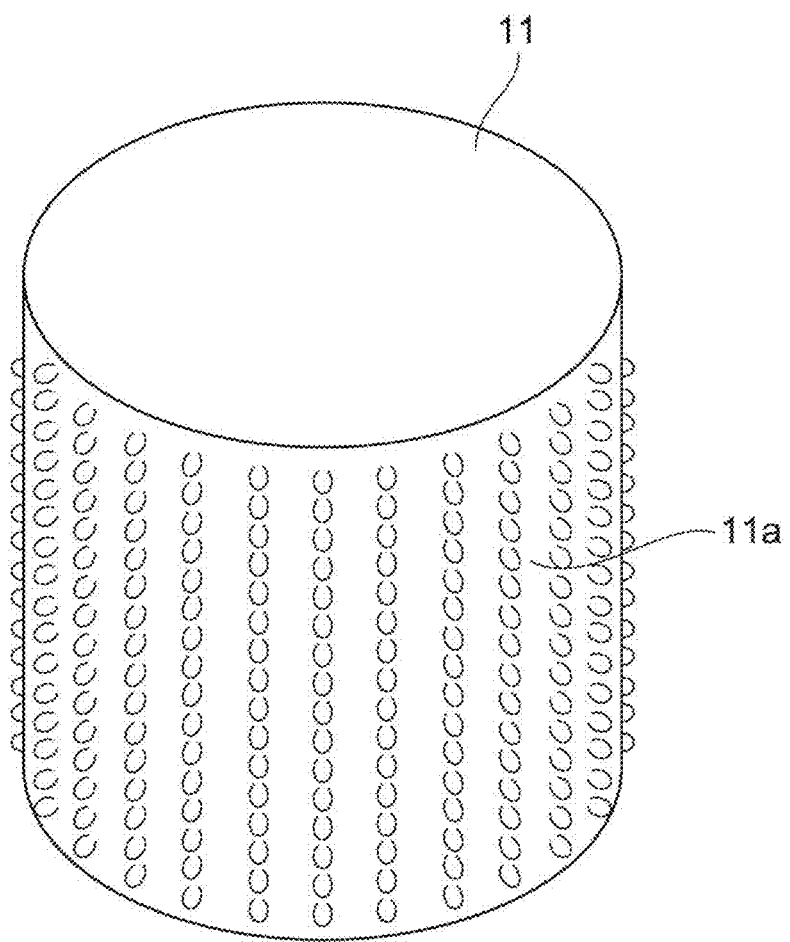
FIG. 28 is a cross-sectional view of a pillar of a second modification example of the surface-enhanced Raman scattering element of one embodiment of the present invention.

Further, the cross-sectional shape of the groove 12 is not limited to a rectangular shape, and may be a U-shape, a V-shape, or the like. Further, if the gap G is formed in the portion corresponding to the groove 12 in the conductor layer 6, the conductor layer 6 may not be formed on the surfaces of the support portion 8 and the substrate 4 (for example, the conductor layer 6 is formed only on the pillar 11 having the groove 12, and the conductor layer 6 may be discontinuous on the surfaces of the support portion 8 and the substrate 4). Further, a recessed region other than the groove 12 may be provided on the outer surface of the projection such as the pillar 11 or the inner surface of the depression such as the hole 15. That is, a shape of the recessed region, such as a recessed region (a concave region, a dented region, or a depressed region) of a cutout portion, a depressed portion, or the like formed on the outer surface of the projection or the inner surface of the depression is not limited. For example, when peaks and valleys are repeated in the side surface 11a of the pillar 11 as illustrated in FIG. 27, portions of valleys are recessed regions. Similarly, when peaks and valleys are repeated in the side surface 15a of the hole 15, valley portions are recessed regions. Further, when a large number of projections are provided on the side surface 11a of the pillar 11 as illustrated in FIG. 28, a portion between adjacent projections is the recessed region. Similarly, when a large number of projections are provided on the side surface 15a of the hole 15, a portion between adjacent projections is the recessed region.

Here, when attention is paid to a pair of adjacent projections (corresponding to the pillars 11), a width of the gap formed in the portion corresponding to the recessed region provided on the outer surface of the projection is smaller than a distance between the conductor layer formed on an outer surface of one of the projections and the conductor layer formed on an outer surface of the other projection. Accordingly, it is possible to easily and stably form narrow gaps (gaps preferably functioning as nanogaps) that cannot be obtained by only a structure of the fine structure portion.

Figure 29:
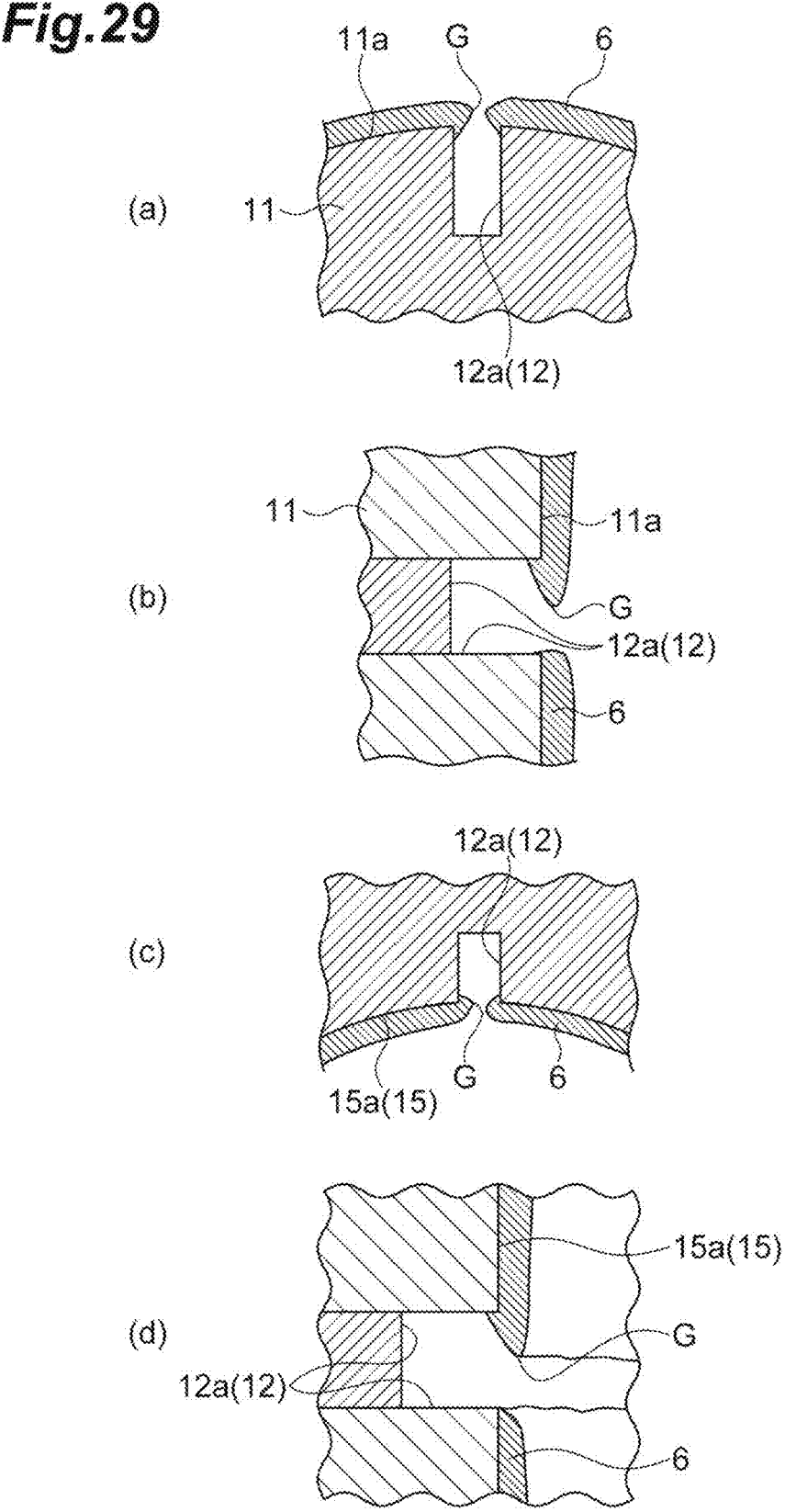
FIG. 29 is a partially enlarged cross-sectional view of a pillar and a hole of a surface-enhanced Raman scattering element according to an embodiment of the present invention.

Further, as illustrated in FIGS. 29(*a*), 29(*b*), 29(*c*) and 29(*d*), the conductor layer 6 separated by the groove 12 is raised (projects) on the opening of the groove 12, and accordingly, an interval of the gap G formed in the opening of the groove 12 may be smaller than the width of the groove 12. FIG. 29(*a*) is a partially enlarged cross-sectional view of the pillar 11 of the first embodiment, FIG. 29(*b*) is a partially enlarged cross-sectional view of the pillar 11 of the second embodiment, FIG. 29(*c*) is a partially enlarged cross-sectional view of the hole 15 of the third embodiment, and FIG. 29(*d*) is a partially enlarged cross-sectional view of the hole 15 of the fourth embodiment.

INDUSTRIAL APPLICABILITY

According to the present invention, it is possible to provide a surface-enhanced Raman scattering element capable of increasing the intensity of surface-enhanced Raman scattering using preferable nanogaps, and the method of manufacturing the same.

REFERENCE SIGNS LIST

3: SERS element (Surface-enhanced Raman scattering element)
4: Substrate
4*a*: Surface
6: Conductor layer
7: Fine structure portion
10: Optical functional portion
11: Pillar (projection)
11*i* a: Side surface (outer surface)
12: Groove (recessed region)
12*a*: Inner surface
15: Hole (depression)
15*a*: Side surface (inner surface)
G: Gap
CL: Center line

The invention claimed is:

1. A surface-enhanced Raman scattering element, comprising:
a substrate;
a fine structure portion formed on a surface of the substrate and having a plurality of projections; and
a conductor layer formed on the fine structure portion and constituting an optical functional portion that causes surface-enhanced Raman scattering,
wherein a recessed region is provided in an outer surface of each of the plurality of projections,
a plurality of gaps are formed in the conductor layer by forming the conductor layer on the outer surface of each of the plurality of projections in a state in which at least a portion of an inner surface of the recessed region is exposed such that the conductor layer is not formed on the portion, and
wherein when viewed from a cross-section of one of the plurality of projections being parallel in a height direction thereof or perpendicular in the height direction thereof, the recessed region is formed such that a straight line along at least a portion of the inner surface of the recessed region passes through two points on the outer surface of the one of the plurality of projections in a distal end side thereof with respect to the surface of the substrate.

2. The surface-enhanced Raman scattering element according to claim 1,
wherein the plurality of projections are periodically arranged along the surface.

3. The surface-enhanced Raman scattering element according to claim 1,
wherein a plurality of recessed regions are provided for one of the projections.

4. The surface-enhanced Raman scattering element according to claim 1,
wherein the recessed region is a groove extending along a center line of the projection.

5. The surface-enhanced Raman scattering element according to claim 1,
wherein the recessed region is a groove extending to surround a center line of the projection.

6. A surface-enhanced Raman scattering element, comprising:
a substrate;
a fine structure portion formed on a surface of the substrate and having a plurality of depressions; and
a conductor layer formed on the fine structure portion and constituting an optical functional portion that causes surface-enhanced Raman scattering,
wherein a recessed region is provided in an inner surface of each of the plurality of depressions,
a plurality of gaps are formed in the conductor layer by forming the conductor layer on the inner surface of each of the plurality of depressions in a state in which at least a portion of an inner surface of the recessed region is exposed such that the conductor layer is not formed on the portion, and
wherein when viewed from a cross-section of one of the plurality of depressions being parallel in a depth direction thereof or perpendicular in the depth direction thereof, the recessed region is formed such that a straight line along at least a portion of the inner surface of the recessed region passes through two points on the one of the plurality of depressions in an opening side thereof with respect to a bottom surface thereof.

7. The surface-enhanced Raman scattering element according to claim 6,
wherein the plurality of depressions are periodically arranged along the surface.

8. The surface-enhanced Raman scattering element according to claim 6,
wherein a plurality of recessed regions are provided for one of the depressions.

9. The surface-enhanced Raman scattering element according to claim 6,
wherein the recessed region is a groove extending along a center line of the depression.

10. The surface-enhanced Raman scattering element according to claim 6,
wherein the recessed region is a groove extending to surround a center line of the depression.

11. A method of manufacturing a surface-enhanced Raman scattering element, the method comprising:
a first step of forming a fine structure portion having a plurality of projections on a surface of a substrate, a recessed region being provided in an outer surface of each of the plurality of projections; and a second step of forming a conductor layer to constitute an optical functional portion causing surface-enhanced Raman scattering on the fine structure portion using vapor phase growth, wherein the second step includes stopping the vapor phase growth in a state in which at least a portion of an inner surface of the recessed region is exposed such that the conductor layer is not formed on the portion, and wherein when viewed from a cross-section of one of the plurality of depressions being parallel in a height direction thereof or perpendicular in the height direction thereof, the recessed region is formed such that a straight line along at least a portion of the inner surface of the recessed region passes through two points on the outer surface of the one of the plurality of projections in a distal end side thereof with respect to the surface of the substrate.

12. The method of manufacturing a surface-enhanced Raman scattering element according to claim 11, wherein the vapor phase growth is vapor deposition.

13. A method of manufacturing a surface-enhanced Raman scattering element, the method comprising:

a first step of forming a fine structure portion having a plurality of depressions on a surface of a substrate, a recessed region being provided in an inner surface of each of the plurality of depressions; and a second step of forming a conductor layer to constitute an optical functional portion causing surface-enhanced Raman scattering on the fine structure portion using vapor phase growth, wherein the second step includes stopping the vapor phase growth in a state in which at least a portion of an inner surface of the recessed region is exposed such that the conductor layer is not formed on the portion, and wherein when viewed from a cross-section of one of the plurality of depressions being parallel in a depth direction thereof or perpendicular in the depth direction thereof, the recessed region is formed such that a straight line along at least a portion of the inner surface of the recessed region passes through two points on the one of the plurality of depressions in an opening side thereof with respect to a bottom surface thereof.

14. The method of manufacturing a surface-enhanced Raman scattering element according to claim 13, wherein the vapor phase growth is vapor deposition.

* * * * *